United States Patent [19]
Castelhano et al.

[11] Patent Number: 6,013,792
[45] Date of Patent: Jan. 11, 2000

[54] MATRIX METALLOPROTEASE INHIBITORS

[75] Inventors: Arlindo Lucas Castelhano, Pleasanton, Calif.; Teng Jiam Liak, Mississauga; Stephen Horne, Burlington, both of Canada; Alexander Krantz, Menlo Park; Zhengyu Yuan, Santa Clara, both of Calif.

[73] Assignee: Syntex (U.S.A.), Inc., Palo Alto, Calif.

[21] Appl. No.: 08/382,818

[22] Filed: Feb. 3, 1995

Related U.S. Application Data

[63] Continuation-in-part of application No. 08/102,655, Aug. 5, 1993, abandoned.

[51] Int. Cl.⁷ .................................................. C07D 245/00
[52] U.S. Cl. .......................................................... 540/460
[58] Field of Search .................................. 540/456, 460; 514/413, 80

[56] References Cited

FOREIGN PATENT DOCUMENTS

WO 93/09136  5/1993  WIPO ................ C07K 5/06

*Primary Examiner*—Mukund J. Shah
*Assistant Examiner*—Bruck Kifle
*Attorney, Agent, or Firm*—Heller Ehrman White & McAuliffe

[57] ABSTRACT

Compounds of formula (I):

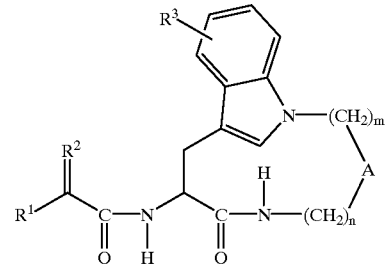

as single stereoisomers or mixtures thereof and their pharmaceutically acceptable salts inhibit matrix metalloproteases, such as interstitial collagenases, and are useful in the treatment of mammals having disease states alleviated by the inhibition of such matrix metalloproteases, for example arthritic diseases or bone resorption disease, such as osteoporosis.

22 Claims, No Drawings

MATRIX METALLOPROTEASE INHIBITORS

CROSS-REFERENCE TO RELATED APPLICATIONS

This application is a continuation-in-part of Ser. No. 08/102,655, filed Aug. 5, 1993, abandoned incorporated herein by reference.

FIELD OF THE INVENTION

The present invention is directed to compounds and their pharmaceutically acceptable salts, which inhibit matrix metalloproteases, particularly interstitial collagenases, and are therefore useful in the treatment of mammals having disease states alleviated by the inhibition of such matrix metalloproteases.

BACKGROUND OF THE INVENTION

Matrix metalloproteases are a family of proteases responsible for degradation and remodeling of connective tissues. Members of this family of enzymes share a number of properties, including zinc and calcium dependence, secretion as zymogens, and 40–50% amino acid sequence homology.

The matrix metalloprotease family includes interstitial collagenases, derived from fibroblasts/macrophages and neutrophils, which catalyze the initial and rate-limiting cleavage of native collagen types I, II, III and X.

Collagen, the major structural protein of mammals, is an essential component of the matrix of many tissues, for example, cartilage, bone, tendon and skin. Interstitial collagenases are very specific matrix metalloproteases which cleave collagen to give two fragments which spontaneously denature at physiological temperatures and therefore become susceptible to cleavage by less specific enzymes. As cleavage by the collagenase results in the loss of structural integrity of the target tissue, it is essentially an irreversible process and therefore a good target for therapeutic intervention.

In addition to interstitial collagenases, the matrix metalloprotease family of enzymes include two distinct, but highly related, gelatinases: a 72-kDa enzyme secreted by fibroblasts and a 92-kDa enzyme released by mononuclear phagocytes. These gelatinases are capable of degrading gelatins (denatured collagens), native collagen types IV and V, fibronectin and insoluble elastin.

The matrix metalloprotease family also includes stromelysins 1 and 2, which are capable of cleaving a broad range of matrix substrates, including laminin, fibronectin, proteoglycans and collagen types IV and IX in their non-helical domains.

Matrilysin (putative metalloprotease or PUMP) is a recently described member of the matrix metalloprotease family. Matrilysin is capable of degrading a wide range of matrix substrates including proteoglycans, gelatins, fibronectin, elastin, and laminin. Its expression has been documented in mononuclear phagocytes, rat uterine explants and sporadically in tumors.

Inhibitors of matrix metalloproteases are considered to provide useful treatments for arthritic diseases, bone resorption disease (such as osteoporosis), the enhanced collagen destruction associated with diabetes, periodontal disease, corneal ulceration, ulceration of the skin, and tumor metastasis. For example, the design and potential use of collagenase inhibitors is described in *J. Enzyme Inhibition* (1987), Vol. 2, pp. 1–22, and in *Drug News & Prospectives* (1990), Vol. 3, No. 8, pp. 453–458. Matrix metalloprotease inhibitors are also the subject of various patents and patent applications, for example, U.S. Pat. Nos. 5,189,178 (Galardy) and 5,183,900 (Galardy), European Published Patent Applications 0 438 223 (Beecham) and 0 276 436 (F. Hoffmann-La Roche), Patent Cooperation Treaty International Applications 92/21360 (Merck), 92/06966 (Beecham) and 92/09563 (Glycomed).

SUMMARY OF THE INVENTION

The invention provides new compounds which are useful an inhibitors of matrix metalloproteases, particularly interstitial collagenases, and which are effective in treating disease states characterized by excessive activity of matrix metalloproteases.

Accordingly, one aspect of the invention is directed to compounds of formula (I) as a single stereoisomer or as a mixture of stereoisomers:

(I)

[Chemical structure shown]

wherein:
m is 3, 4, 5, or 6; and
n is 0, 1, 2, 3, or 4; such that:
when m is 3 or 4; and n is 1, 2, 3, or 4; then
A is $-CH_2-$, $-O-$, or $-N(R^{11})-$, where $R^{11}$ is hydrogen or alkyl;
$R^1$ is a) $-CH_2-R^4$ where $R^4$ is mercapto, acetylthio, carboxy, hydroxyaminocarbonyl, N-hydroxyformylamino, alkoxycarbonyl, aryloxycarbonyl, aralkoxycarbonyl, benzyloxyaminocarbonyl, or

[Chemical structure with P(=O)(OH) and S-R^6]

in which $R^6$ is optionally substituted aryl, wherein the aryl group is quinol-2-yl, naphth-1-yl, naphth-2-yl, pyridyl or phenyl;

b) $-CH(R^7)-R^8$ where $R^7$ is alkyl, hydroxy, amino, alkylamino, arylamino, alkylsulphonylamino, aralkylsulphonylamino, alkoxycarbonyl, aminocarbonyl, or carboxy; or $R^7$ is $-CH_2NHR$, where R is hydrogen, alkyl, aryl, 2-benzoxazole, $-SO_2R^a$, $-SO_2NHR^a$, $-SO_2OR^a$, $-C(O)R^a$ $-C(O)NHR^a$, $-C(O)OR^a$, where $R^a$ is alkyl, trifluoroethyl, aryl, or aralkyl; and $R^8$ is carboxy, hydroxyaminocarbonyl, alkoxycarbonyl or aralkoxycarbonyl; or C) $-NH-CH(R^9)-R^{10}$ where $R^9$ is hydrogen, alkyl or aralkyl, and $R^{10}$ is carboxy, alkoxycarbonyl or aralkoxycarbonyl, phosphonyl, dialkylphosphonyl, or methoxyphosphonyl;

$R^2$ is alkyl, trifluoromethylalkyl, cycloalkyl, cycloalkylalkyl, or aralkyl; and $R^3$ is hydrogen, halo, alkyl or alkoxy;

or:

when n is 0; and m is 4, 5 or 6; then

A is —CH($R^{12}$)— where $R^{12}$ is carboxy, alkoxycarbonyl or optionally substituted carbamoyl; and $R^1$, $R^2$ and $R^3$ are as defined above; or a pharmaceutically acceptable salt thereof.

Another aspect of the invention is directed to methods of inhibiting matrix metalloprotease activity in a mammal, which methods comprise administering to the mammal in need thereof a therapeutically effective amount of a compound of formula (I), or a pharmaceutically acceptable salt thereof.

Another aspect of the invention is directed to pharmaceutical compositions useful in inhibiting matrix metalloprotease activity in a mammal, which composition comprises a therapeutically effective amount of a compound of formula (I), or a pharmaceutically acceptable salt thereof; and a pharmaceutically acceptable excipient.

DETAILED DESCRIPTION OF THE INVENTION

Definitions

As used in the specification and appended claims, unless specified to the contrary, the following terms have the meaning indicated:

"BOC" refers to t-butoxycarbonyl.

"CBZ" refers to benzyloxycarbonyl (carbobenzyloxy).

"DMF" refers to N,N-dimethylformamide.

"EDCI" refers to N-ethyl-N'-(3-dimethylaminopropyl)-carbodiimide.

"HOBT" refers to 1-hydroxybenzotriazole.

"Pht" refers to phthalimide.

"Acetylthio" refers to the radical —SC(O)CH$_3$.

"Halo" refers to bromo, chloro or fluoro.

"Alkyl" refers to a straight or branched chain monovalent radical consisting solely of carbon and hydrogen, having from one to six carbon atoms and containing no unsaturation, e.g., methyl, ethyl, n-propyl, 2-methylpropyl (iso-butyl), 1-methylethyl (iso-propyl), 1,1-dimethylethyl (t-butyl), and the like, or containing at least one unsaturated bond, e.g., ethenyl, pent-4-enyl and the like.

"Alkylamino" refers to a radical of the formula —NHR$_a$. wherein R$_a$ is alkyl as defined above, e.g. methylamino, ethylamino, n-propylamino, and the like.

"Alkylene" as used herein means a branched or unbranched saturated divalent hydrocarbon radical containing 1 to 6 carbon atoms, such as methylene, ethylene, propylene, 2-methylpropylene, 1,2-dimethylpropylene, hexylene, and the like.

"Alkoxy" refers to a radical of the formula —OR$_a$ wherein R$_a$ is alkyl as defined above, e.g., methoxy, ethoxy, n-propoxy, i-propoxy, 1-methylethoxy, n-butoxy, t-butoxy, and the like.

"Aryl" refers to a monovalent unsaturated aromatic carbocyclic radical having one or two rings, such as phenyl, naphthyl, or biphenyl, or to a monovalent unsaturated aromatic heterocyclic radical such as quinolyl, pyridyl, phthalimido, or thienyl optionally substituted with aryl as defined herein. Aryl can optionally be mono-, di- or tri-substituted independently with hydroxy, lower alkyl, lower alkoxy, chloro, fluoro, trifluoromethyl and/or cyano. e.g., 6-nitroquinol-2-yl, 6-fluoroquinol-2-yl, 6-hydroxyquinol-2-yl, 6-methoxyquinol-2-yl, 6-nitronaphth-1-yl, 6-chloronaphth-1-yl, 6-hydroxynaphth-1-yl, 6-methoxynaphth-1-yl, 6-nitronaphth-2-yl, 6-chloronaphth-2-yl, 6-hydroxynaphth-2-yl, 6-methoxynaphth-2-yl, 6-nitrophenyl, 6-chlorophenyl, 6-hydroxyphenyl, 6-methoxyphenyl, biphenyl, 3-methylpyridyl, 4-ethylpyridyl and the like.

"Aryloxy" refers to a radical of the formula —OR$_b$ wherein R$_b$ is aryl as defined above, e.g., phenoxy, quinol-2-yloxy, naphth-1-yloxy, or naphth-2-yloxy, and the like.

"Aralkyl" refers to a radical of the formula —R$_c$R$_b$ wherein R$_c$ is alkylene as defined above and R$_b$ is aryl as defined above, e.g., benzyl, phenylethylene, 3-phenylpropyl, and the like.

"Aralkoxy" refers to a radical of the formula —OR$_c$R$_b$ wherein R$_c$ is alkylene as defined above and R$_b$ is aryl as defined above, e.g., benzyloxy, 3-naphth-2-ylpropoxy, and the like.

"Alkoxycarbonyl" refers to a radical of the formula —C(O)OR$_b$ wherein R$_b$ is alkyl as defined above, or R$_b$ is a saturated carbocyclic ring containing one or more heteroatoms e.g., methoxycarbonyl, ethoxycarbonyl, t-butoxycarbonyl, N-methylpiperid-4-yl-oxycarbonyl, and the like.

"Aralkoxycarbonyl" refers to a radical of the formula —C(O)R$_d$ wherein R$_d$ is aralkoxy as defined above, e.g., benzyloxycarbonyl, naphthyl-2-ylethoxycarbonyl, and the like.

"Benzyloxyaminocarbonyl" refers to the radical of the formula —C(O)NHOCH$_2$Ph wherein Ph is phenyl.

"Carbamoyl" refers to the radical —C(O)NH$_2$.

"Carboxy" refers to the radical —C(O)OH.

"Cycloalkyl" refers to a monovalent saturated carbocyclic radical containing no unsaturation and having from three to six carbon atoms, e.g. cyclopropyl, cyclobutyl, cyclopentyl, cyclohexyl.

"Cycloalkylalkyl" refers to a radical of the formula —(CH$_2$)$_p$R$_c$ where R$_c$ is cycloalkyl as defined above and p is an integer of 1–6, e.g. cyclopentylpropyl, cyclopropylmethyl, cyclobutylmethyl, cyclohexylbutyl.

"Hydroxyamino" refers to the radical —NHOH.

"Hydroxyaminocarbonyl" refers to the radical —C(O) NHOH.

"N-hydroxyformylamino" refers to the radical —N(OH)C(O)H.

"Mercapto" refers to the radical —SH.

"Sulfonyl" refers to the radical =S(O)$_2$

"Phosphonyl" refers to the radical —PO(OH)$_2$

"Optional" or "optionally" means that the subsequently described event of circumstances may or may not occur, and that the description includes instances where said event or circumstance occurs and instances in which it does not. For example, "optionally substituted quinol-2-yl" means that the quinol-2-yl radical may or may not be substituted and that the description includes both substituted quinol-2-yl radicals and quinol-2-yl radicals having no substitution.

"optionally substituted carbamoyl" refers to a carbamoyl radical optionally substituted on the nitrogen atom by one or more substituents selected from the group consisting of alkyl, mono- and di-alkylaminoalkyl, and aralkyl.

"Amino-protecting group" as used herein refers to those organic groups intended to protect nitrogen atoms against undesirable reactions during synthetic procedures, and includes, but is not limited to, benzyl, acyl, acetyl, benzyloxycarbonyl (carbobenzyloxy), p-methoxybenzyloxycarbonyl, p-nitrobenzyloxycarbonyl, t-butoxycarbonyl, and the like.

"Pharmaceutically acceptable salt" includes both pharmaceutically acceptable acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethamine, dicyclohexylamine, choline and caffeine.

"Mammal" includes humans and all domestic and wild animals, including, without limitation, cattle, horses, swine, sheep, goats, dogs, cats, and the like.

"Therapeutically effective amount" refers to that amount of a compound of formula (I) which, when administered to a mammal in need thereof, is sufficient to effect treatment, as defined below, for disease-states alleviated by the inhibition of matrix metalloprotease activity, particularly interstitial collagenase activity. The amount of a compound of formula (I) which constitutes a "therapeutically effective amount" will vary depending on the compound, the disease-state and its severity, and the mammal to be treated, but can be determined routinely by one of ordinary skill in the art having regard to his own knowledge and to this disclosure.

"Treating" or "treatment" as used herein cover the treatment of a disease state in a mammal, particularly in a human, which disease state is alleviated by the inhibition of matrix metalloprotease activity, particularly interstitial collagenase activity, and the like; and include:

(i) preventing the disease-state from occurring in a mammal, in particular, when such mammal is predisposed to the disease state but has not yet been diagnosed as having it;

(ii) inhibiting the disease-state, i.e., arresting its development; or (iii) relieving the disease-state, i.e., causing regression of the disease state.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

"Diastereoisomers" are stereoisomers which are not mirror-images of each other.

The nomenclature used herein is basically a modified form of I.U.P.A.C. nomenclature wherein compounds of the invention are named as derivatives of phosphinic or alkanoic acids having a tricylo substituent. The compounds of formula (I) have at least two asymmetric carbon atoms in their structure; i.e. at the point of attachment of the $R^2$ substituent and the indolylmethyl group. The compounds of formula (I) and their pharmaceutically acceptable salts may therefore exist as single enantiomers, racemates, diastereoisomers, and as mixtures of enantiomers and diastereomers. All such single stereoisomers, racemates, diasteroisomers, and mixtures thereof, are intended to be within the scope of this invention.

When naming the single stereoisomers of compounds of formula (I) an absolute descriptor, R or S, may be assigned to the chiral carbon atoms therein according to the "Sequence Rule" procedure of Cahn, Ingold and Prelog.

For example, the following compound of formula (I) wherein n is 2; m is 3; A is —$CH_2$—; $R^1$ is —$CH_2$—$R^4$ where $R^4$ is —C(O)NHOH; $R^2$ is 2-methylpropyl and $R^3$ is hydrogen, i.e., the compound of the following formula:

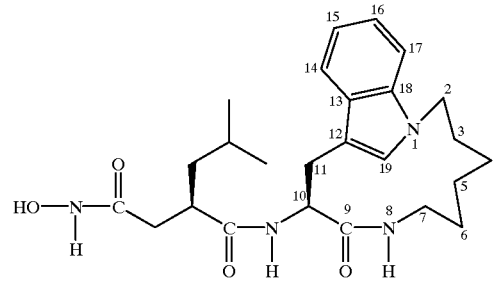

is named herein as (3R, 10S)-N-hydroxy-5-methyl-3-(9-oxo-1,8-diaza-tricyclo[10.6.1.0$^{13,18}$]nonadeca-12(19),13 (18),14,16-tetraen-10-ylcarbamoyl)hexanamide.

Utility and Administration

A. Utility

The compounds of formula (I) are useful in inhibiting mammalian matrix metalloproteases, particularly mammalian interstitial collagenases, thereby preventing the degradation of collagen within the mammal. The compounds are therefore useful in treating disease states which are associated with increased activity of matrix metalloproteases, particularly increased activity of interstitial collagenase, such as arthritis and osteoarthritis, tumor metastasis, periodontal disease and corneal ulcerations. See, e.g., *Arthritis and Rheumatism* (1993), Vol. 36, No. 2, pp. 181–189; *Arthritis and Rheumatism* (1991), Vol. 34, No. 9, pp. 1073–1075; *Seminars in Arthritis and Rheumatism* (1990), Vol. 19, No. 4, Supplement 1 (February), pp. 16–20; *Drugs of the Future* (1990), Vol. 15, No. 5, pp. 495–508; and *J. Enzyme Inhibition* (1987), Vol. 2, pp. 1–22.

B. Testing

The ability of the compounds of formula (I) to inhibit matrix metalloprotease activity, particularly interstitial collagenase activity, may be demonstrated by a variety of in vitro and ex vivo assays known to those of ordinary skill in the art. For example, the activity of the individual metalloprotease may be demonstrated in the in vitro assay described in *Anal. Biochem.* (1985), Vol. 147, p. 437, or modifications thereof. Physiological effects of the inhibition of matrix metalloproteases may be demonstrated by the ex vivo bovine cartilage explant assay described in *Methods of Enzymology* (1987), Vol. 144, pp. 412–419, or modifications thereof; or by the ex vivo rat fetal long bone assay described in *Proc. Natl. Acad. Sci. USA* (1988), Vol. 85, pp. 8761–8765, or modifications thereof, or in *J. Clin. Invest.* (1965), Vol. 44, pp. 103–116, or modifications thereof.

C. General Administration

Administration of the compounds of formula (I), or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of formula (I) as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of formula (I), or a pharmaceutically acceptable salt thereof, and 99% to 1% by weight of a suitable pharmaceutical excipient. Preferably, the composition will be about 5% to 75% by weight of a compound(s) of formula (I), or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of formula (I), or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of formula (I), or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of formula (I) (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa. 1990). The composition to be administered will, in any event, contain a therapeutically effective amount of a compound of formula (I), or a pharmaceutically acceptable salt thereof, for treatment of a disease-state alleviated by the inhibition of matrix metalloprotease in accordance with the teachings of this invention.

The compounds of formula (I), or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-state, and the host undergoing therapy. Generally, a therapeutically effective daily dose is from about 0.14 mg to about 14.3 mg/kg of body weight per day of a compound of formula (I), or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of formula (I), or a pharmaceutically acceptable salt thereof, preferably from about 50 mg to about 700 mg per day, and most preferably from about 100 mg to about 500 mg per day.

Preferred Embodiments

Preferred are the compounds of formula (I) where n is 1, 2 or 3, m is 3, and A is —CH$_2$—. A preferred subgroup of compounds of this group are those compounds where n is 1 or 2, where R$^1$ is —CH$_2$—R$^4$ and R$^3$ is hydrogen, especially where R$^2$ is 2-methylpropyl, biphenylpropyl, thien-2-yl-ethyl, cyclopentyl, cyclopropylmethyl, or cyclopentylmethyl; and R$^4$ is carboxy, alkoxycarbonyl, N-hydroxyaminocarbonyl, or N-hydroxyformylamino.

A preferred subclass of compounds of this class are those compounds wherein R$^2$ is 2-methylpropyl or cyclopentylmethyl, and R$^4$ is carboxy, N-hydroxyaminocarbonyl, or N-hydroxyformylamino, or where R$^4$ is mercapto or acetylthio.

Another preferred subgroup included those compounds wherein R$^1$ is

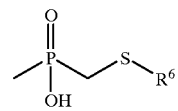

where R$^6$ is optionally substituted aryl, wherein the aryl group is quinol-2-yl, naphth-1-yl, naphth-2-yl, pyridyl or phenyl. A preferred subclass of compounds of this class are those compounds wherein R$^6$ is quinol-2-yl.

Another preferred class of compounds of the subgroup are those compounds wherein $R^1$ is —CH($R^7$)—$R^8$ where $R^7$ is —CH$_2$NHR, especially where R is hydrogen, $R^2$ is 2-methylpropyl or cyclopentylmethyl, $R^3$ is hydrogen, and $R^8$ is carboxy. Particularly preferred are those compounds where R is methoxycarbonyl, methanesulfonyl, or ethylureido.

Another preferred class of compounds of the subgroup are those compounds wherein $R^1$ is —CH($R^7$)—$R^8$ where $R^7$ is alkyl, alkoxycarbonyl or carboxy; and $R^2$ is 2-methylpropyl or cyclopentylmethyl; $R^3$ is hydrogen; and $R^8$ is carboxy or hydroxyaminocarbonyl. A preferred subclass of compounds of this class are those compounds wherein $R^7$ is methoxycarbonyl.

Another preferred class of compounds of the subgroup are those compounds wherein $R^1$ is —NH—CH($R^9$)—$R^{10}$ where $R^9$ is hydrogen, alkyl or aralkyl; and $R^{10}$ is carboxy, alkoxycarbonyl or aralkoxycarbonyl.

Another preferred class of compounds are those compounds wherein n is 2 or 3; m is 4; A is —N($R^{11}$)— where $R^{11}$ is hydrogen or alkyl; $R^2$ is alkyl; and $R^3$ is hydrogen. A preferred class of compounds of this subgroup are those compounds wherein n is 2, $R^2$ is 2-methylpropyl, and $R^{11}$ is methyl.

Presently, the most preferred compounds of formula (I) are the following:

(3R,10S)-N-hydroxy-5-methyl-3-(9-oxo-1,8-diazatricyclo-[10.6.1.0$^{13,18}$]nonadeca-12(19),13(18),14,16-tetraen-10-ylcarbamoyl)hexanamide;

(3R,11S)-N-hydroxy-5-methyl-3-(10-oxo-1,9-diazatricyclo-[11.6.1.0$^{14,19}$]eicosa-13(20),14(19),15,17-tetraen-11-ylcarbamoyl)hexanamide;

(3R,9S)-N-hydroxy-5-methyl-3-(8-oxo-1,7-diazatricyclo-[9.6.1.0$^{12,19}$]octadeca-11(18),12(17),13,15-tetraen-9-ylcarbamoyl)hexanamide;

(3R,9S)-5-methyl-3-(8-oxo-1,7-diazatricyclo[9.6.1.0$^{12,17}$] octadeca-11(18),12(17),13,15-tetraen-9-ylcarbamoyl) hexanoic acid;

(3R,9S)-4-cyclopentyl-3-(8-oxo-1,7-diazatricyclo [9.6.1.0$^{12,17}$]octadeca-11(18),12(17),13,15-tetraen-9-ylcarbamoyl)butanoic acid;

(3R,9S)-2-(methanesulfonamidomethyl)-4-cyclopentyl-3-(8-oxo-1,7-diazatricyclo[9.6.1.0$^{12,17}$]octadeca-11(18),12 (17),13,15-tetraen-9-ylcarbamoyl)butanoic acid;

(10S)-2-mercaptomethyl-4-methyl-N-(9-oxo-1,8-diazatricyclo-[10.6.1.0$^{13,18}$]nonadeca-12(19),13(18),14, 16-tetraen-10-ylcarbamoyl)pentanamide;

(10S)-4-methyl-2-(9-oxo-1,8-diazatricyclo-[10.6.1.0$^{13,18}$] nonadeca-12(19),13(18),14,16-tetraen-10-ylcarbamoyl) pentyl(quinolin-2-ylthiomethyl)phosphinic acid;

(10S)-2-acetylthiomethyl-4-methyl-N-(9-oxo-1,8-diazatricyclo-[10.6.1.0$^{13,18}$]nonadeca-12(19),13(18),14, 16-tetraen-10-ylcarbamoyl)pentanamide;

(3R,10S)-N-hydroxy-5-methyl-2-methoxycarbonyl-3-(9-oxo-1,8-diazatricyclo-[10.6.1.0$^{13,18}$]nonadeca-12(19),13 (18),14,16-tetraen-10-ylcarbamoyl)hexanamide;

(3R,10S)-4-cyclopentyl-3-(9-oxo-1,8-diazatricyclo [10.6.1.0$^{13,18}$]-nonadeca12(19),13(18),14,16-tetraen-10-ylcarbamoyl)butanoic acid;

(3R,10S)-4-cyclopentyl-3-(9-oxo-1,8-diazatricyclo [10.6.1.0$^{13,18}$]-nonadeca12(19),13(18),14,16-tetraen-10-ylcarbamoyl)butanoic acid ethyl ester;

(3R,10S)-5-methyl-3-(9-oxo-1,8-diazatricyclo [10.6.1.0$^{13,18}$])-nonadeca-12(19),13(18),14,16-tetraen-10-ylcarbamoyl)hexanoic acid 1-(2-dimethylaminoethyl) amide;

(3R,10S)-5-methyl-3-(9-oxo-1,8-diazatricyclo [10.6.1.0$^{13,18}$]-nonadeca-12(19),13(18),14,16-tetraen-10-ylcarbamoyl)hexanoic acid 1-methylpiperidin-4-yl ester;

(3R,10S)-3-cyclopentyl-3-(9-oxo-1,8-diazatricyclo [10.6.1.0$^{13,18}$]nonadeca-12(19),13(18),14,16-tetraen-10-ylcarbamoyl)propionic acid;

(3R,10S)-4-cyclopropyl-3-(9-oxo-1,8-diazatricyclo [10.6.1.0$^{13,18}$]nonadeca-12(19),13(18),14,16-tetraen-10-ylcarbamoyl)butanoic acid;

(3R,10S)-6-(biphenyl-4-yl)-3-(9-oxo-1,8-diazatricyclo-[10.6.1.0$^{13,18}$]-nonadeca12(19),13(18),14,16-tetraen-10-ylcarbamoyl)hexanoic acid;

(3R,10S)-3-(9-oxo-1,8-diazatricyclo[10.6.1.0$^{13,18}$] nonadeca-12(19),13(18),1$^4$,16-tetraen-10-ylcarbamoyl)-5-(thiophen-2-yl)pentanoic acid;

(3R,10S)-2-(aminomethyl)-5-methyl-3-(9-oxo-1,8-diazatricyclo[10.6.1.0$^{13,18}$]nonadeca-12(19),13(18),14,16-tetraen-10-ylcarbamoyl)hexanoic acid;

(3R,10S)-N-hydroxy-N-formylamino-5-methyl-3-(9-oxo-1,8-diazatricyclo-[10.6.1.0$^{13,18}$]nonadecal2(19),13(18),14, 16-tetraen-10-ylcarbamoyl)hexanoic acid;

(3R,10S)-2-(methoxycarbonylaminomethyl)-5-methyl-3-(9-oxo-1,8-diazatricyclo[10.6.1.0$^{13,18}$]nonadeca-12(19), 13(18),14,16-tetraen-10-ylcarbamoyl)hexanoic acid;

(3R,10S)-2-(methanesulfonamidomethyl)-5-methyl-3-(9-oxo-1,8-diazatricyclo-[10.6.1.0$^{13,18}$]nonadeca-12(19),13 (18),14,16-tetraen-10-ylcarbamoyl)-hexanoic acid;

(3R,10S)-2-(3-ethylureidomethyl)-5-methyl-3-(9-oxo-1,8-diazatricyclo-[10.6.1.0$^{13,18}$]nonadeca-12(19),13(18),14, 16-tetraen-10-ylcarbamoyl)hexanoic acid; and (3RS,10S)-N-hydroxy-N-formyl-5-methyl-3-(9-oxo-1,8-diaza-tricyclo[10.6.1.0$^{13,18}$]nonadeca-12(19),13(18),14, 16-tetraen-10-ylcarbamoyl)hexylamine.

Preparation of Compounds of Formula (I)

Compounds of formula (I) are peptide derivatives which can be prepared from the constituent α-amino acid derivative. Standard methods for the formation of peptide bonds are further illustrated by M. Bodanszky et al., *The Practice of Peptide Synthesis* (1984), Springer-Verlag; M. Bodanszky, *Principles of Peptide Synthesis* (1984), Springer-Verlag; J. P. Greenstein et al., *Chemistry of the Amino Acids* (1961), Vol. 1–3, John Wiley and Sons Inc.; G. R. Pettit, *Synthetic Peptides* (1970), Vol. 1–2, Van Nostrand Reinhold Company.

Amide couplings used to form the compounds of formula (I) are generally performed by the carbodiimide method with reagents such as dicyclohexylcarbodiimide or N'-ethyl-N'-(3-dimethylaminopropyl)-carbodiimide (EDCI) in the presence of 1-hydroxybenzotriazole (HOBT) in an inert solvent such as dimethylformamide (DMF). Other methods of forming the amide or peptide bond include, but not limited to synthetic routes via an acid chloride, acyl azide, mixed anhydride or activated ester such as nitrophenyl ester. Typically, solution phase amide couplings with or without peptide fragments are performed.

The selection of protecting groups for the terminal amino or carboxy groups of compounds used in the preparation of the compounds of formula (I) is dictated in part by the particular amide or peptide coupling conditions, and in part by the amino acid and/or peptide components involved in the coupling. Amino-protecting groups commonly used include those which are well-known in the art, for example, benzyloxycarbonyl (carbobenzyloxy), p-methoxybenzyloxycarbonyl, p-nitrobenzyloxycarbonyl, t-butoxycarbonyl (BOC), and the like. It is preferred to use either BOC or benzyloxycarbonyl (CBZ) as the protecting group for the α-amino group because of the relative ease of its removal by mild acids, e.g., by trifluoroacetic acid (TFA) or hydrochloric acid in ethyl acetate; or by catalytic hydrogenation.

The individual stereoisomers of compounds of formula (I) may be separated from each other by methods known to those of ordinary skill in the art, e.g., where $R^1$ is carboxy, by separation (e.g. fractional crystallization, chromatography, and/or by the methods disclosed herein) of the diastereomeric salts formed by the reaction of a compound of formula (I) with an optically active base, at temperatures between 0° C. and the reflux temperature of the solvent employed for fractional crystallization. Exemplary of such optically active bases are brucine, strychnine, quinine, quinidine, cinchonidine, ephedrine, α-methylbenzylamine, and the like.

Combinations of substituents and/or variables in the compounds of formula (I) are permissible only if such combinations result in stable compounds. A. Preparation of Intermediates: Compounds of Formula (J)

Compounds of formula (J):

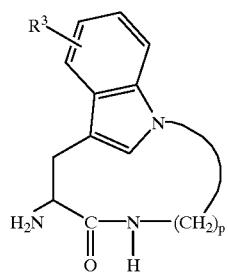

(J)

where $R^3$ is as defined in the Summary of the Invention, and p is 5, 6, 7 or 8, are useful for the preparation of compounds of formula (I). Compounds of formula (J) are prepared as shown in Reaction Scheme 1 below; $R^3$ and p are as defined, BOC is t-butoxycarbonyl, and $R^{13}$ is hydrogen, mesyl or tosyl.

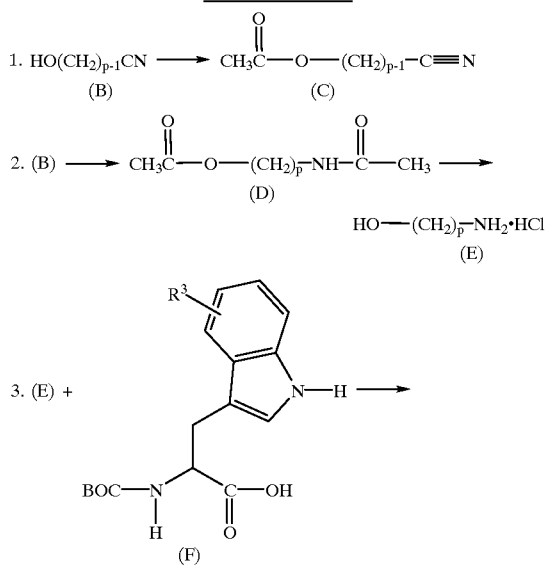

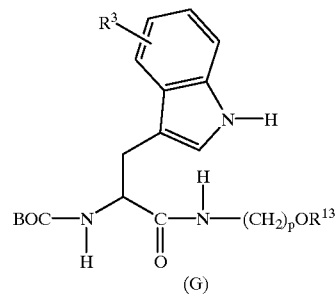

(G)

4. (G) ⟶

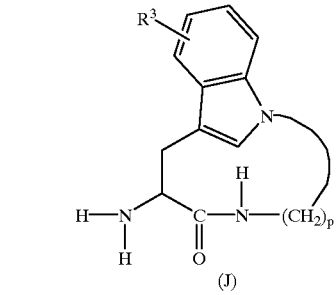

(H)

⟶

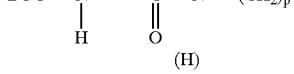

(J)

Compounds of formulae (B) and (F) are commercially available, e.g., from Karl Industries, Inc. or Sigma, respectively, or may be prepared by methods known to those skilled in the art.

In general, compounds of formula (J) are prepared by first esterifying an alcohol of formula (B) with acetic anhydride in the presence of a base, preferably pyridine, to form a compound of formula (C), which is then reduced in the presence of acetic anhydride to form a compound of formula (D). The compound of formula (D) is hydrolyzed under acidic conditions, preferably hydrochloric acid, to form a compound of formula (E), which is then coupled with a compound of formula (F) under standard peptide coupling conditions, for example, with EDCI in the presence of HOBT in DMF, to form a compound of formula (G) wherein $R^{13}$ is hydroxy. This compound may then be treated with either tosyl chloride or mesyl chloride to form a compound of formula (G) wherein $R^{13}$ is mesyl or tosyl. Cyclization of the tosylates so formed with an excess of NaH in an inert solvent, preferably THF, under high dilution at room temperature yields the compounds of formula (H). The protecting group on the compounds of formula (H) is removed under mild acidic conditions, preferably in the presence of trifluoroacetic acid, to yield compounds of formula (J).

B. Preparation of Compounds of Formulae (Ia), (Ib), (Ic) and (Id)

Compounds of formula (Ia) are compounds of formula (I) where n is 1, 2 or 3; m is 3 or 4; A is —$CH_2$—; $R^1$ is —$CH_2$—$R^4$ where $R^4$ is alkoxycarbonyl; and $R^2$ and $R^3$ are as defined in the Summary of the Invention.

Compounds of formula (Ib) are compounds of formula (I) where n is 1, 2 or 3; m is 3 or 4; A is —$CH_2$—; $R^1$ is —$CH_2$—$R^4$ where $R^4$ is carboxy; and $R^2$ and $R^3$ are as defined in the Summary of the Invention.

Compounds of formula (Ic) are compounds of formula (I) where n is 1, 2 or 3; m is 3 or 4; A is —$CH_2$—; $R^1$ is —$CH_2$—$R^4$ where $R^4$ is benzyloxyaminocarbonyl; and $R^2$ and $R^3$ are as defined in the Summary of the Invention.

Compounds of formula (Id) are compounds of formula (I) where n is 1, 2 or 3; m is 3 or 4; A is —$CH_2$—; $R^1$ is —$CH_2$—$R^4$ where $R^4$ is hydroxyaminocarbonyl; and $R^2$ and $R^3$ are as defined in the Summary of the Invention.

Compounds of formula (Ia), (Ib), (Ic) and (Id) are prepared as shown in Reaction Scheme 2 below, where p is 5, 6, 7 or 8; $R^{14}$ is t-butyl or benzyl; $R^{7a}$ is hydrogen or alkoxycarbonyl; and $R^2$ and $R^3$ are as defined in the Summary of the Invention.

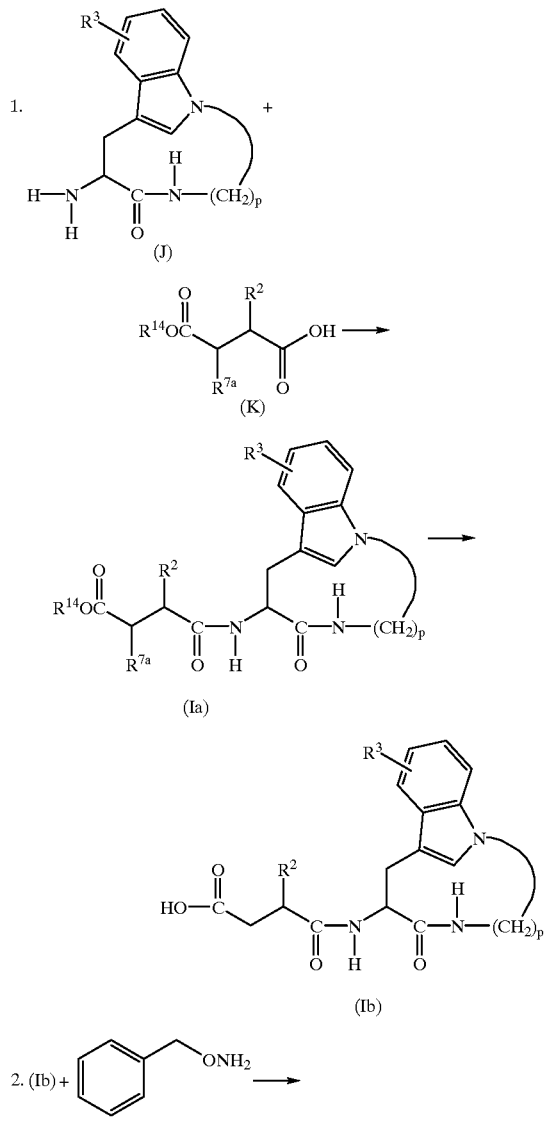

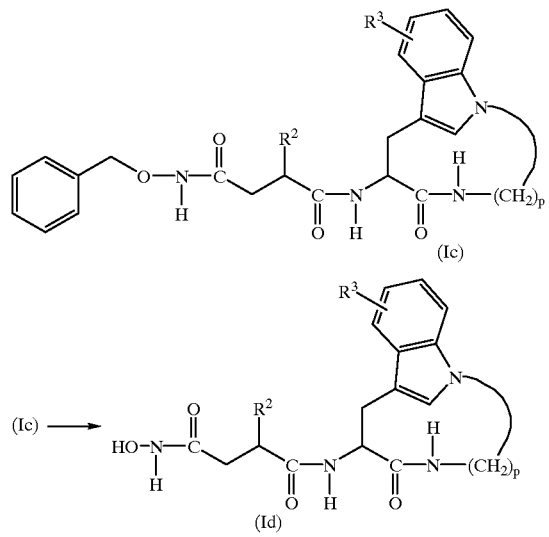

Compounds of formula (K) are prepared by methods described herein or may be prepared by methods known to those of ordinary skill in the art.

In general, compounds of formulae (Ia), (Ib) and (Ic) are prepared by first coupling a compound of formula (J) with a compound of formula (K) under standard peptide coupling conditions to form a compound of formula (Ia). The protecting group in the compound of formula (Ia) is then removed under mild acidic conditions to yield a compound of formula (Ib).

A compound of formula (Ib) is then coupled with O-benzylhydroxylamine under standard peptide coupling conditions to yield a compound of formula (Ic). The benzyl protecting group in the compound of formula (Ic) is then removed under catalytic hydrogenation conditions to yield a compound of formula (Id).

C. Preparation of Compounds of Formula (Ie) and (If)

Compounds of formula (Ie) are compounds of formula (I) wherein n is 1, 2, or 3; m is 3 or 4; A is —$CH_2$—; $R^1$ is —$CH_2$—$R^4$ where $R^4$ is acetylthio; and $R^2$ and $R^3$ are as defined in the Summary of the Invention.

Compounds of formula (If) are compounds of formula (I) wherein n is 1, 2, or 3; m is 3 or 4; A is —$CH_2$—; $R^1$ is —$CH_2$—$R^4$ where $R^4$ is mercapto; and $R^2$ and $R^3$ are as defined in the Summary of the Invention.

Compounds of formulae (Ie) and (If) are prepared as shown in the following Reaction Scheme 3 where $R^2$ and $R^3$ are as defined above and p is 5, 6, 7 or 8:

Reaction Scheme 3

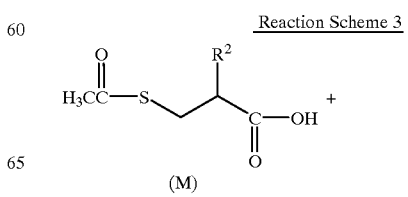

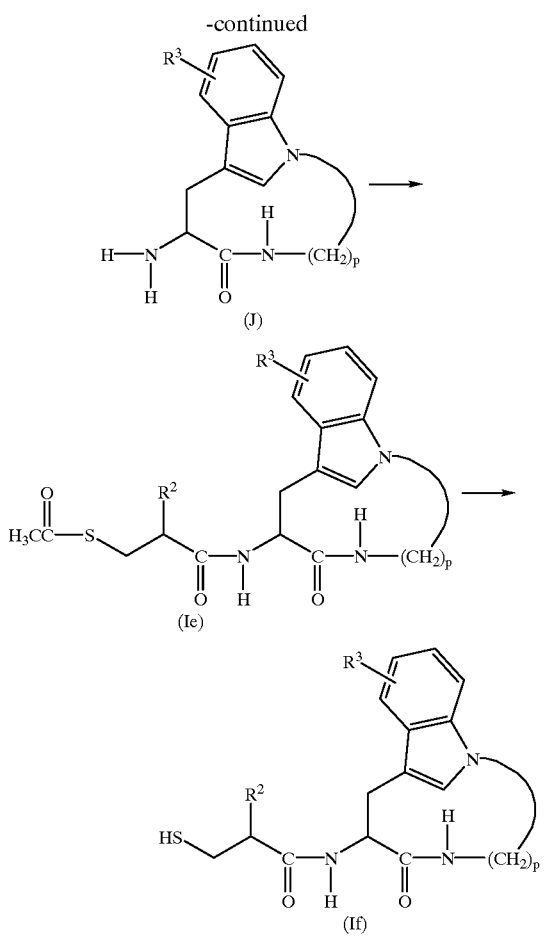

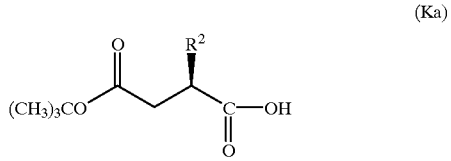

wherein $R^{7a}$ is hydrogen, is a stereoisomer of a compound of formula (K) that has an R configuration. Compounds of formula (Ka) are prepared as shown in the following Reaction Scheme 4 wherein $R^2$ is as defined above:

Reaction Scheme 4

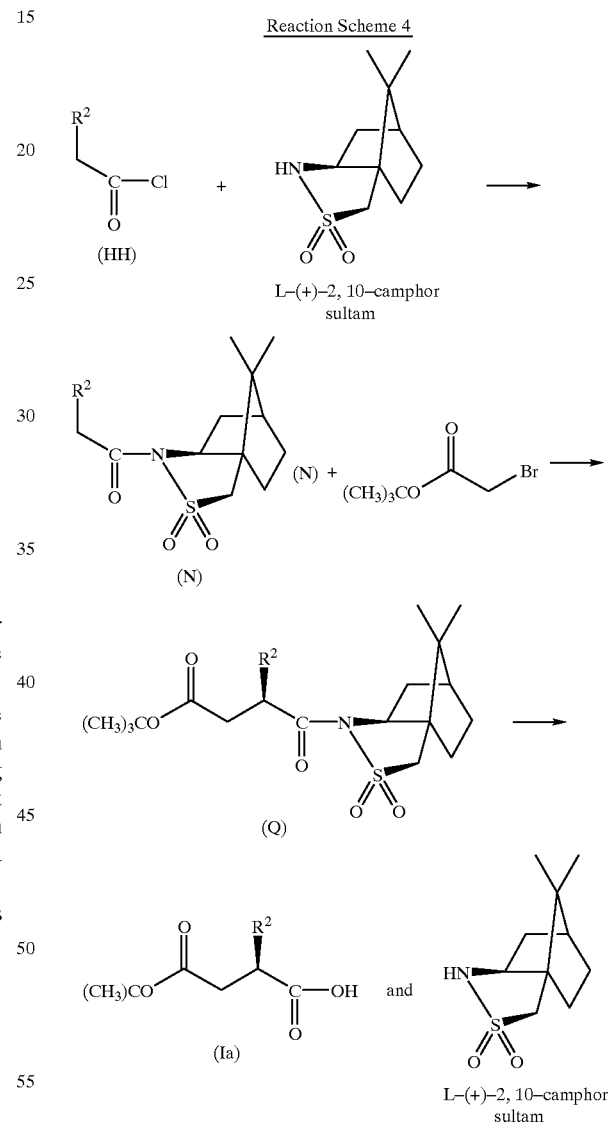

Compounds of formula (M) are commercially available or may be prepared by methods known to those skilled in the art.

In general, compounds of formulae (Ie) and (If) are prepared by first coupling a compound of formula (M) with a compound of formula (J) under standard peptide coupling conditions to yield a compound of formula (Ie). Treatment of compounds of formula (Ie) with concentrated $NH_4OH$ in methanol yields the corresponding compounds of formula (If).

D. Preparation of Individual Stereoisomers of Compounds of Formula (K)

Compounds of formula (K):

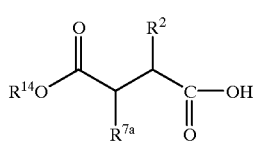

wherein $R^{14}$ is t-butyl or benzyl and $R^{7a}$ is hydrogen, alkoxycarbonyl, hydroxycarbamoyl, carboxy or optionally substituted carbamoyl, are used in the preparation of compounds of formula (I). Individual stereoisomers of compounds of formula (K) are used in the preparation of the corresponding stereoisomer of compounds of formula (I). In particular, compounds of following formula (Ka):

In a similar manner, but substituting D-(−)-2,10-camphor sultam for L-(+)-2,10-camphor sultam, the corresponding individual stereoisomers in the S configuration are prepared.

Compounds of formula (HH) are commercially available or may be prepared according to methods known to those of ordinary skill in the art, for example, by the method described in Example 11 below. L-(+)-2,10-Camphor sultam and D-(−)-2,10-camphor sultam are commercially available, for example, from Aldrich.

In general, compounds of formula (Ka) are prepared by first condensing a compound of formula (HH) with L-(+)-2,10-camphor sultam to form a compound of formula (N). Using NaHMDS to generate the anion for 1 hour, the reaction is quenched with the t-butylbromoacetate to form the corresponding ester of formula (Q). The camphor group is then removed under basic conditions to yield an individual stereoisomer of a compound of formula (Ka) wherein the carbon to which the $R^2$ substituent is attached is in the R configuration.

Compounds of formula (Kb):

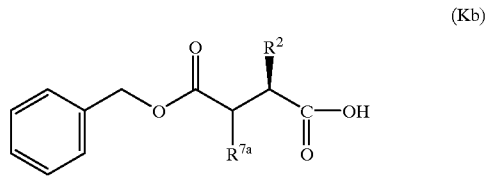

(Kb)

wherein $R^{7c}$ is alkoxycarbonyl, may be prepared as shown in the following Reaction Scheme 5 wherein $R^2$ and $R^{7c}$ are as defined above:

Reaction Scheme 5

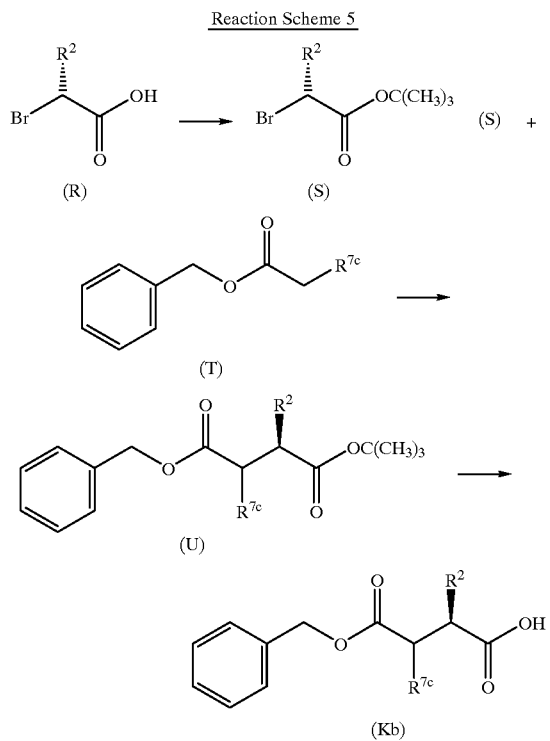

Compounds of formula (R) and (T) are commercially available or may be prepared according to methods known to those skilled in the art.

In general, compounds of formula (Kb) are prepared by first treating a compound of formula (R) with isobutene and a catalytic amount of concentrated $H_2SO_4$ in methylene chloride followed by distillation to yield a t-butyl ester of formula (S). The compound of formula (S) is then reacted with a compound of formula (T) in the presence of potassium t-butoxide to yield the compound of formula (U). Hydrolysis of the compound of formula (U) under acidic conditions, preferably with trifluoroacetic acid at room temperature, yields the compound of formula (Kb) where $R^{7c}$ is alkoxycarbonyl.

Compounds of formula (K) where $R^{7a}$ is carboxy may be prepared from compounds of formula (Kb) where $R^{7c}$ is alkoxycarbonyl by methods known to those of ordinary skill in the art, e.g. hydrolysis.

In addition to the above described methods of preparing isomers of formula (K), compounds of formula (K) wherein $R^{7a}$ is alkyl may be prepared by treating a compound of formula (K) wherein $R^{7a}$ is hydrogen in an aprotic solvent, for example, THF, in the presence of $NaN(TMS)_2$ with an haloalkane, preferably iodomethane, to yield a compound of formula (K) wherein $R^{7a}$ is alkyl.

E. Preparation of Compounds of Formula (Ig)

Compounds of formula (Ig) are compounds of formula (I) wherein n is 1, 2 or 3; m is 3 or 4; A is —$CH_2$—; $R^1$ is —$CH_2$—$R^4$ where R4 is

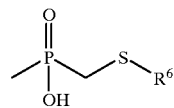

in which $R^6$ is optionally substituted aryl, wherein the aryl group is quinol-2-yl, naphth-1-yl, naphth-2-yl, pyridyl or phenyl; $R^2$ is alkyl and $R^3$ is hydrogen. Compounds of formula (Ig) are prepared as shown in the following Reaction Scheme 6 wherein p is 5, 6, 7 or 8; $R^2$, $R^3$ and $R^6$ are as defined above and $R^{12a}$ is mesyl or tosyl:

Reaction Scheme 6

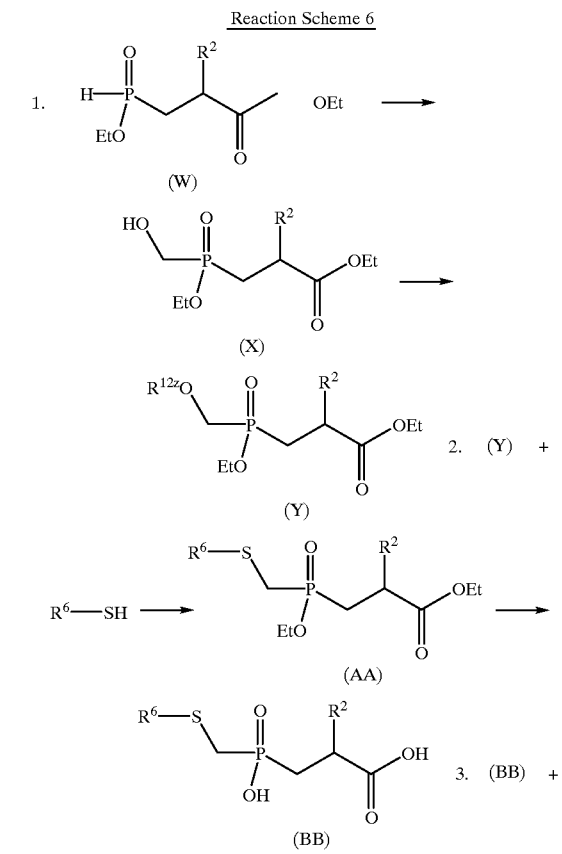

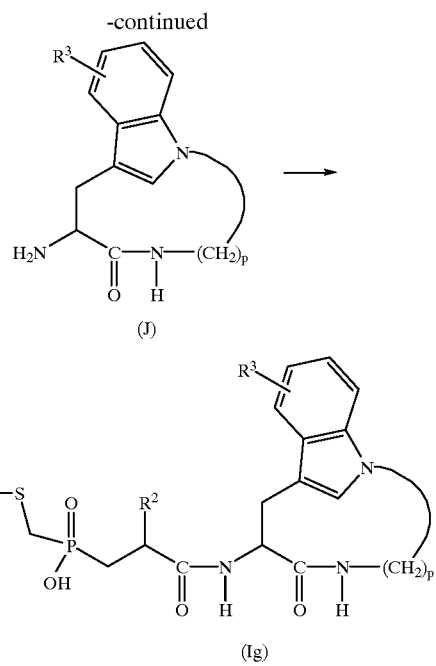

where Et represents ethyl.

Compounds of formula (W) may be prepared according to methods known to those of ordinary skill in the art or may be prepared according to the method described in Example 19 below. Compounds of formula (Z) are commercially available or may be prepared according to methods known to those of ordinary skill in the art.

In general, compounds of formula (Ig) are prepared by first treating a compound of formula (W) with formamide to form a compound of formula (X). The compound of formula (X) is then treated with tosyl or mesyl chloride under basic conditions to form a compound of formula (Y). The compound of formula (Y) is then reacted with a salt of a compound of formula (Z) (preferably the sodium salt formed from the reaction of the compound of formula (Z) with sodium hydride) to form a compound of formula (AA). The compound of formula (AA) is then hydrolyzed under basic conditions to form a compound of formula (BB). The compound of formula (BB) is then coupled with a compound of formula (J) under standard peptide conditions, preferably with 1,1'-carbonyldiimidazole, to form a compound of formula (Ig).

F. Preparation of Compounds of Formulae (Ih), (Ii) and (Ij)

Compounds of formulae (Ih), (Ii) and (Ij) are compounds of formula (Ib), formula (Ic) and formula (Id), respectively, as described above in Section B, wherein the indole ring is completely saturated. They are prepared as shown in the following Reaction Scheme 7 wherein $R^2$ and $R^3$ are as defined in the Summary of the Invention, $R^{7a}$ is hydrogen and p is 5, 6, 7 or 8:

Reaction Scheme 7

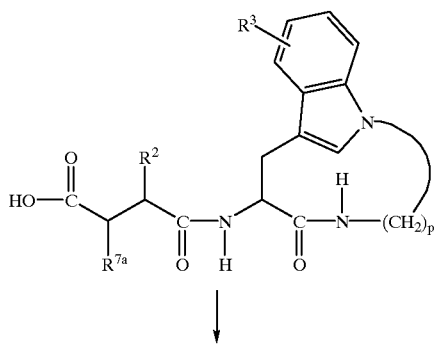

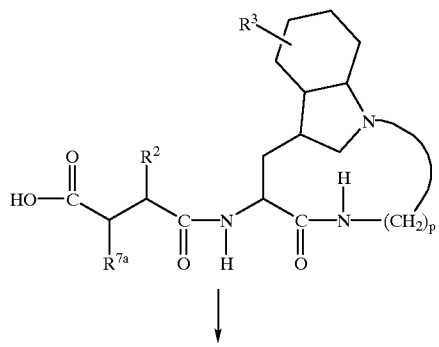

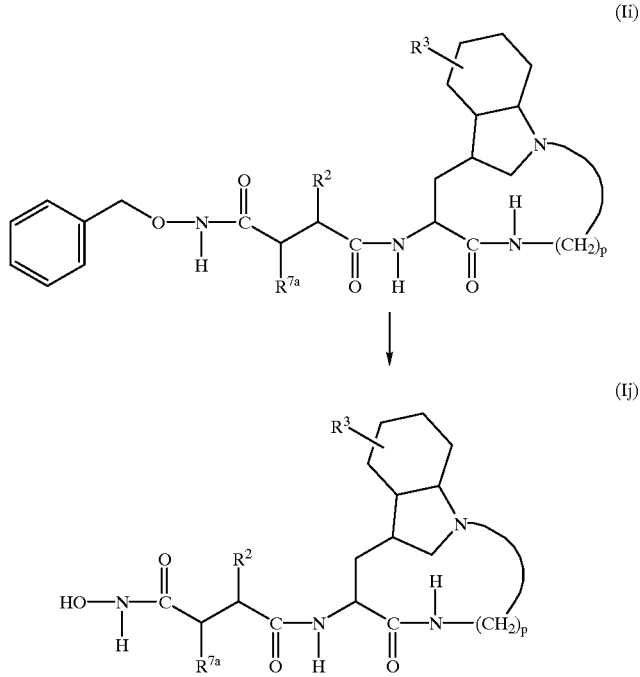

In general, compounds of formulae (Ih), (Ii) and (Ij) are prepared by first reducing a compound of formula (Ib) under catalytic hydrogenation conditions to form a compound of formula (Ih). The compound of formula (Ih) is then reacted with O-benzyihydroxylamine under standard peptide coupling conditions to yield a compound of formula (Ii). The benzyl protecting group is then removed from the compound of formula (Ii) under catalytic hydrogenation conditions to yield a compound of formula (Ij).

G. Preparation of Compounds of Formulae (Ik), (Il), (Im) and (In)

Compounds of formula (Ik) are compounds of formula (I) with an allylic bond, wherein n is 2 or 3; m is 4; A is —$NR^{11}$ where $R^{11}$ is hydrogen or alkyl; $R^1$ is —$CH_2$—$R^4$ where $R^4$ is t-butoxycarbonyl; and $R^2$ and $R^3$ are as defined in the Summary of the Invention.

Compounds of formula (Il) are compounds of formula (I) with an allylic bond, wherein n is 2 or 3; m is 4; A is —$NR^{11}$ where $R^{11}$ is hydrogen or alkyl; $R^1$ is —$CH_2$—$R^4$ where $R^4$ is carboxy; and R2 and $R^3$ are as defined in the Summary of the Invention.

Compounds of formula (Im) are compounds of formula (I) with an allylic bond, wherein n is 2 or 3; m is 4; A is —$NR^{11}$ where $R^{11}$ is hydrogen or alkyl; $R^1$ is —$CH_2$—$R^4$ where $R^4$ is benzyloxyaminocarbonyl; and $R^2$ and $R^3$ are as defined in the Summary of the Invention.

Compounds of formula (In) are compounds of formula (I) where n is 2 or 3; m is 4; A is —$NR^{11}$ where $R^{11}$ is hydrogen or alkyl; $R^1$ is —$CH_2$—$R^4$ where $R^4$ is hydroxyaminocarbonyl; and $R^2$ and $R^3$ are as defined in the Summary of the Invention.

Compounds of formula (Ik), (Il), (Im) and (In) are prepared as shown in the following Reaction Scheme 8 where n is 2 or 3; $R^2$, $R^3$ and $R^{11}$ are as defined above; $R^{14}$ is t-butyl; $R^{7a}$ is hydrogen; and BOC is t-butoxycarbonyl:

Reaction Scheme 8

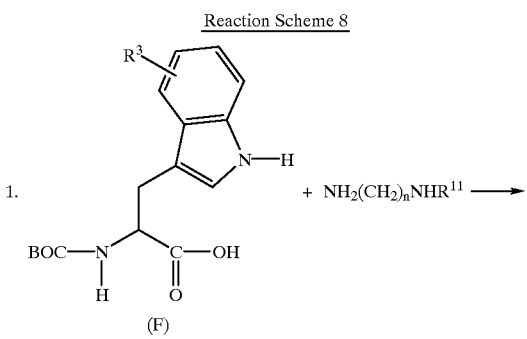

-continued
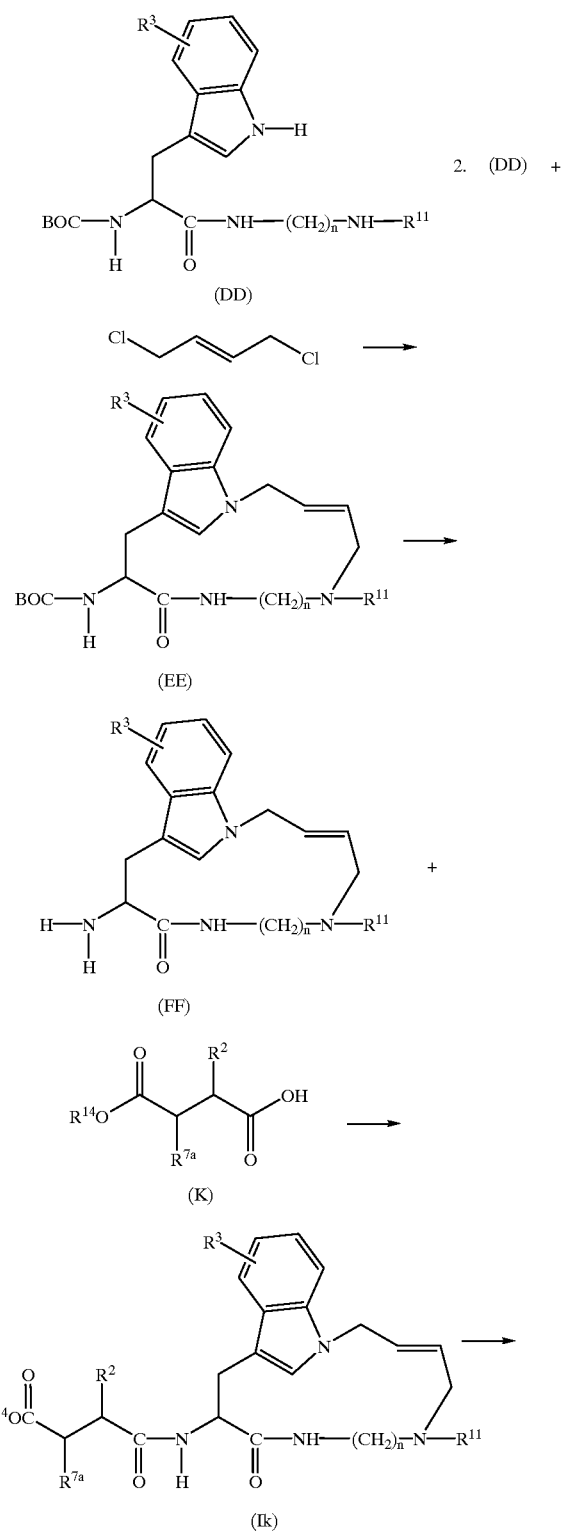

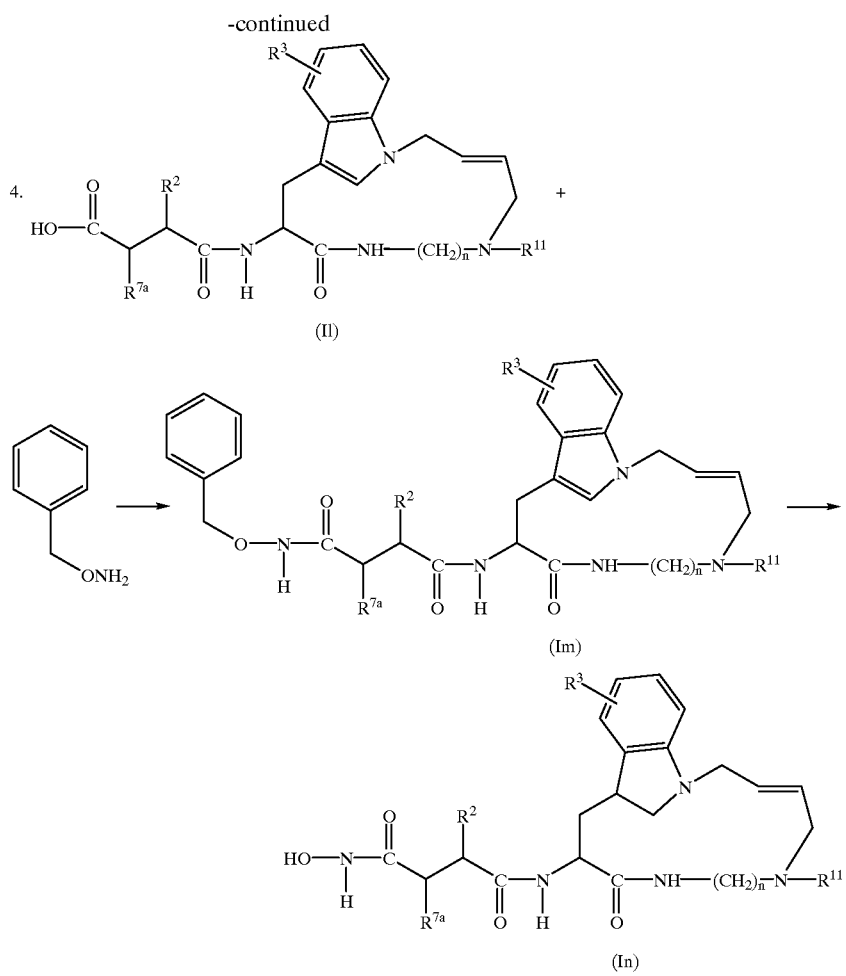

Compounds of formula (K) are prepared by methods known to those of ordinary skill in the art or by the methods described herein.

In general, compounds of formulae (Ik), (Il), (Im) and (In) are prepared by first reacting a compound of formula (P) with a diaminealkane or mono-alkyl substituted diaminealkane under standard peptide coupling conditions, for example, with HOBT and EDCI, in an inert solvent, for example, DMF, to form a compound of formula (DD). The compound of formula (DD) is then reacted with trans-1,4-dichlorobut-2-ene under basic conditions to form a compound of formula (EE). The amino-protecting group of the compound of formula (EE) is then removed under mild acidic conditions, preferably with trifluoroacetic acid, to form a compound of formula (FF).

The compound of formula (FF) is then coupled with a compound of formula (K) under standard peptide coupling conditions, for example, with HOBt and EDCI, to form a compound of formula (Ik). The protecting group of the compound of formula (Ik) is then removed under mildly acidic conditions, for example, with trifluoroacetic acid, to yield a compound of formula (Il). The compound of formula (Il) is then treated with O-benzylhydroxylamine under standard peptide coupling conditions to yield a compound of formula (Im). The protecting group of formula (Im) is then removed under catalytic hydrogenation conditions to yield a compound of formula (In).

H. Preparation of Compounds of Formulae (Io) and (Ip)

Compounds of formula (Io) are compounds of formula (I) wherein n is 1, 2 or 3; m is 3 or 4; A is —CH$_2$—; R$^1$ is —NH—CH(R$^9$)—R$^{10}$ where R$^9$ is hydrogen, alkyl or aralkyl, and R$^{10}$ is aralkoxycarbonyl; and R$^2$ and R$^3$ are as defined in the Summary of the Invention.

Compounds of formula (Ip) are compounds of formula (I) wherein n is 1, 2 or 3; m is 3 or 4; A is —CH$_2$—; R$^1$ is —NH—CH(R$^9$)—R$^{10}$ where R$^9$ is hydrogen, alkyl or aralkyl, and R$^{10}$ is carboxy; and R$^2$ and R$^3$ are as defined in the Summary of the Invention.

Compounds of formulae (Io) and (Ip) are prepared as shown in the following Reaction Scheme 9 wherein p is 5, 6, 7 or 8; and R$^2$, R$^3$ and R$^9$ are as defined above:

Reaction Scheme 9

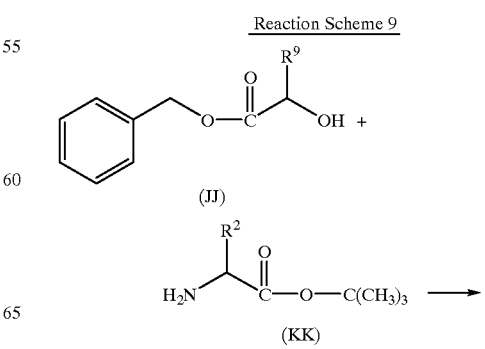

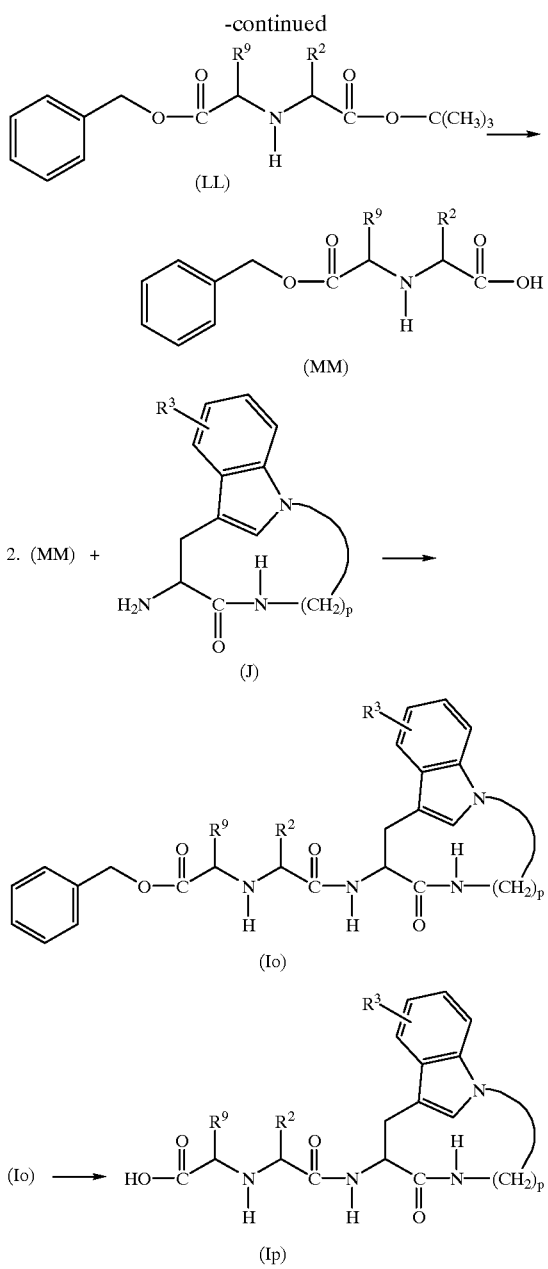

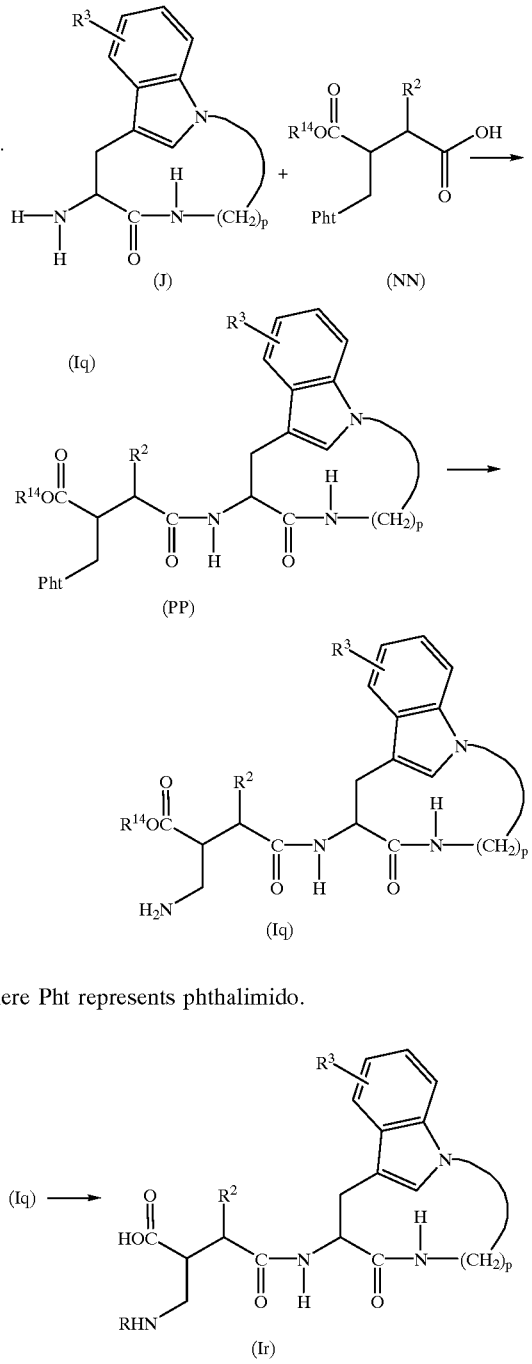

hydrogen, and $R^1$ is benzyloxycarbonyl or t-butyloxycarbonyl, and $R^2$ and $R^3$ are as defined in the Summary of the Invention.

Compounds of formula (Ir) are compounds of formula (I) wherein n is 1, 2 or 3; m is 3 or 4; A is —$CH_2$—; $R^1$ is —$CH(R^7)$—$R^8$, where $R^7$ is —$CH_2NHR$, $R^8$ is carboxyl, and R, $R^2$, and $R^3$ are as defined in the Summary of the Invention.

Compounds of formulae (Iq) and (Ir) are prepared as shown in Reaction Scheme 10 below.

where Pht represents phthalimido.

Compounds of formula (JJ) are prepared by methods known to those of ordinary skill in the art or by the method described in Example 36 below.

In general, compounds of formulae (Il) and (Im) are prepared by first treating a compound of formula (JJ) with triflic anhydride, followed by treatment with a compound of formula (KK) under basic conditions to form a compound of formula (LL). The compound of formula (LL) is then hydrolyzed under mildly acidic conditions, preferably with trifluoroacetic acid, to form a compound of formula (MM). The compound of formula (MM) is then coupled with a compound of formula (J) under standard peptide coupling conditions to form a compound of formula (Io). The compound of formula (Io) is then deprotected to form a compound of formula (Ip).

I. Preparation of Compounds of Formulae (Iq) and (Ir)

Compounds of formula (Iq) are compounds of formula (I) wherein n is is 1, 2 or 3; m is 3 or 4; A is —$CH_2$—; $R^1$ is —$CH(R^7)$—$R^8$, where $R^7$ is —$CH_2NHR$, in which R is Compounds of formula (J) are prepared by methods shown above. Compounds of Formula (NN) are prepared by methods well known to those skilled in the art, for example as described in EP 575844.

In general, compounds of formulae (PP) and (Iq) are prepared by first coupling a compound of formula (J) with a compound of formula (NN) under standard peptide coupling conditions to form a compound of formula (PP). The phthalimido group of the compound of formula (PP) is then converted into an amine by standard methods, for example treatment with hydrazine, to give a compound of formula (Iq).

The compound of Formula (Iq) may then be converted into a compound of formula (Ir) by reactions well known in the art. For example, reaction of a compound of formula (Iq) with an alkylsulfonyl halide in the presence of a base, followed by hydrolysis of the product with trifluoroacetic acid, gives a compound of formula (Ir) where R is alkylsulfonyl. Similarly, reaction of (Iq) with an alkyl, aryl, or arylalkyl chloroformate gives the corresponding carbamate, reaction with an acyl halide gives the corresponding amide, reaction with an appropriately substituted isocyanate gives the corresponding urea, etc.

J. Preparation of Compounds of Formula (I) where $R^1$ is —$CH_2$—$R^4$, in which $R^4$ is N-hydroxyformylauino To prepare compounds of formula (I) where $R^1$ is —$CH_2$—$R^4$, in which $R^4$ is N-hydroxyformylamino, a compound of formula (J) is first reacted, under the peptide coupling conditions described above, with a compound of the formula:

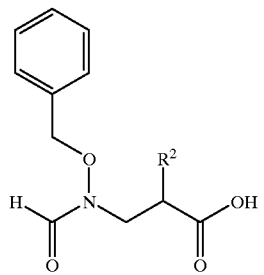

Such compounds may be prepared as shown in U.S. patent application Ser. No. 08/343,158, the complete disclosure of which is hereby incorporated by reference.

The producy of this coupling reaction is then debenzylated in a manner similar to that shown in Reaction Scheme II above, to give a compound of formula (I) where $R^1$ is —$CH_2$—$R^4$, in which $R^4$ is N-hydroxyformylamino.

Salts of Compounds of Formula (I)

In addition, all compounds of formula (I) that exist in free base form may be converted to their pharmaceutically acceptable salts by treatment with the appropriate inorganic or organic acid. Salts of the compounds of formula (I) can also be converted to the free base form or to another salt.

In summary, compounds of formulae (Ia), (Ib), (Ic), (Id), (Ie), (If), (Ig), (Ih), (Ii), (Ij), (Ik), (Il), (Im), (In), (Io) (Ip), (Iq), and (Ir), which are all compounds of formula (I), are prepared by:

1. reacting a compound of formula (K) where $R^{7a}$ is hydrogen or alkoxycarbonyl; and $R^{14}$ is t-butyl or benzyl; with a compound of formula (J) wherein p is 5, 6, 7 or 8; to form a compound of formula (Ia) where p, $R^2$, R3, $R^{7a}$ and $R^{14}$ are as defined for compounds of formulae (K) and (J);
2. treating a compound of formula (Ia) where p is 5, 6, 7 or 8; $R^{7a}$ is hydrogen or alkoxycarbonyl; and $R^{14}$ is t-butyl or benzyl; to form a compound of formula (Ib) where p, $R^2$, $R^3$, and $R^{7a}$ are as defined for the compound of formula (Ia);
3. treating a compound of formula (Ib) where p is 5, 6, 7 or 8; and $R^{7a}$ is hydrogen or alkoxycarbonyl; with O-benzylhydroxylamine to form a compound of formula (Ic) where p, $R^2$, $R^3$, and $R^{7a}$ are as defined for the compound of formula (Ib);
4. treating a compound of formula (Ic) where p is 5, 6, 7 or 8; and $R^{7a}$ is hydrogen or alkoxycarbonyl; to form a compound of formula (Id) where p, $R^2$, $R^3$, and $R^{7a}$ are as defined for the compound of formula (Ic);
5. reacting a compound of formula (M) with a compound of formula (J) where p is 5, 6, 7 or 8; and $R^3$ is hydrogen, to form a compound of formula (Ie) where p, $R^2$ and $R^3$ are as defined for the compounds of formulae (M) and (J);
6. treating a compound of formula (Ie) where p is 5, 6, 7 or 8; and $R^3$ is hydrogen, to form a compound of formula (If) where p, $R^2$, $R^3$ are as defined for the compound of formula (Ie);
7. reacting a compound of formula (BB) where $R^2$ is alkyl; and $R^6$ is optionally substituted aryl wherein the aryl group is quinol-2-yl, naphth-1-yl, naphth-2-yl and phenyl; with a compound of formula (J) where p is 5,6, 7 or 8; and $R^3$ is hydrogen, to form a compound of formula (Ig) where p, $R^2$, $R^3$, and $R^6$ are as defined for the compounds of formulae (BB) and (J);
8. treating a compound of formula (Ib) where p is 5, 6, 7 or 8; to form a compound of formula (Ih) where p, $R^2$ and $R^3$ are as defined for the compound of formula (Ib);
9. treating a compound of formula (Ih) where p is 5, 6, 7 or 8; to form a compound of formula (Ii) where p, $R^2$ and $R^3$ are as defined for the compound of formula (Ih);
10. treating a compound of formula (Ii) where p is 5, 6, 7 or 8; to form a compound of formula (Ij) where p, $R^2$ and $R^3$ are as defined for the compound of formula (Ii);
11. reacting a compound of formula (FF) where n is 2 or 3; and $R^{11}$ is hydrogen or alkyl; with a compound of formula (K) where $R^{7a}$ is hydrogen; and $R^{14}$ is t-butyl, to form a compound of formula (Ik) where n, $R^2$, $R^3$, $R^{7a}$, $R^{11}$ and $R^{14}$ are as defined for the compounds of formulae (FF) and (K);
12. treating a compound of formula (Ik) where n is 2 or 3; $R^{7a}$ is hydrogen; $R^{11}$ is hydrogen or alkyl; and $R^{14}$ is t-butyl, to form a compound of formula (Il) where n, $R^2$, $R^3$, $R^{7a}$ and $R^{11}$ are as defined for the compound of formula (Ik);
13. treating a compound of formula (Il) where n is 2 or 3; $R^{7a}$ is hydrogen; and $R^{11}$ is hydrogen or alkyl; with O-benzylhydroxylamine to form a compound of formula (Im) where n, $R^2$, $R^3$, $R^{7a}$ and $R^{11}$ are as defined for the compound of formula (Il);
14. treating a compound of formula (Im) where n is 2 or 3; $R^{7a}$ is hydrogen; and $R^{11}$ is hydrogen or alkyl, to form a compound of formula (In) where n, $R^2$, $R^3$, $R^{7a}$ and $R^{11}$ are as defined for the compound of formula (GG);
15. reacting a compound of formula (MM) where $R^9$ is hydrogen, alkyl or aralkyl; with a compound of formula (J) where p is 5, 6, 7 or 8; to form a compound of formula (Io) where p, $R^2$, $R^3$, and $R^9$ are as defined for the compounds of formulae (MM) and (J); and
16. treating a compound of formula (Io) where p is 5, 6, 7 or 8; and $R^9$ is hydrogen, alkyl or aralkyl, to form a compound of formula (Ip) where p, $R^2$, $R^3$, and $R^9$ are as defined for the compound of formula (Io).

The following specific examples are provided as a guide to assist in the practice of the invention, and are not intended as a limitation on the scope of the invention.

EXAMPLE 1

Compound of Formula (E)

A. 6-Cyano-1-hexanol (7.1 g, 55.8 mmol) was dissolved in 30 mL of acetic anhydride under argon atmosphere. To this material was added 5.3 mL (65.4 mmol) of pyridine dropwise and the mixture was left to stir for 2 hours. The contents of the flask were then poured into a beaker containing 50 mL of ice water and the material was stirred for 15 minutes. The mixture was transferred to a 250 mL separatory funnel and ether (100 mL) was added. After shaking the ether phase was isolated and the aqueous phase washed twice more with ether (2 ×100 mL). The combined ether phase was washed with brine, dried (MgSO$_4$) and filtered. Evaporation (rotary evaporator and vacuum pump) provided 6-cyano-1-acetoxyhexane (the compound of formula (C)) which was used immediately in the next step.

B. 6-Cyano-1-acetoxy-hexane (55.8 mmol) was dissolved in about 100 mL of acetic anhydride in a Parr reaction bottle (500 mL capacity). To this was added acetic acid (0.5 mL) followed by platinum oxide (100 mg). The flask was placed on a PARR hydrogenator apparatus and charged with hydrogen gas (40 psi). The material was shaken for 12 hours, filtered through celite (to remove catalyst), charged with fresh platinum oxide (100 mg) and hydrogen (40 psi) and left to shake for a further 24 hours. The material was filtered through celite and all volatiles were removed under reduced pressure (rotary evaporator). The desired 1-acetoxy-7-acetamidoheptane was pure enough to use in the next step (11.8 g obtained).

C. 1-Acetoxy-7-acetamidoheptane (11.8 g, 54.3 mmol) was dissolved in 20 mL of methanol in a 200 mL round bottom flask. To this was added 50 mL of 40% aqueous hydrochloric acid and the mixture was heated at reflux for 60 hours. All volatiles were removed under reduced pressure. The desired 7-amino-1-heptanol was obtained as the crystalline hydrochloride salt, m.p. 74–81° C., MS: 131 (MH$^+$).

EXAMPLE 2

Compounds of Formula (G)

A. N-Methylmorpholine (2.2 mL, 19.7 mmol) was added dropwise at room temperature to 7-amino-1-heptanol hydrochloride salt (3.3 g, 19.7 mmol), in 50 mL of dry DMF under argon with stirring. After stirring for 5 minutes the following were added: N-t-butoxycarbonyl-L-tryptophan, (5 g, 16.45 mmol), 1-hydroxybenzotriazole, (2.52 g, 16.45 mmol) and EDCI hydrochloride (4.73 g, 24.7 mmol). The mixture was stirred for 2 hours and then the DMF removed under reduced pressure. The residue was taken up in cold 2.5% HCl (100 mL) and ethyl acetate (3×100 mL) and transferred to a separatory funnel. The organic phase was isolated and washed consecutively with cold 2.5% HCl (100 mL) and then brine (100 mL). The ethyl acetate phase was dried (MgSO$_4$), filtered and concentrated to obtain N-t-butoxycarbonyl-L-tryptophan-(7-hydroxyheptyl)amide; IR (neat): 3300, 2921, 1685, 1645, 1490, 1356, 1157 cm$^{-1}$; $^1$H NMR (80 MHz, CDCl$_3$): δ 0.98–1.62 (m, 10H, —(CH$_2$)$_5$—), 1.45 (s, 9H, t-butyl), 2.86–3.32 (m, 4H,CH—CH$_2$, HN—CH$_2$), 3.68 (t, 2H, J=5.6 Hz, —CH$_2$OH), 4.22–4.55 (m, 1H, CH), 5.12–5.32 (broad d, 1H, NH—CH), 5.65–5.9 (broad t, 1H, NH—CH$_2$), 6.98–7.92 (m, 5H, ArH), 8.63 (broad 8, indole NH).

B. A solution of N-t-butoxycarbonyl-L-tryptophan-(7-hydroxyheptyl)amide (8.2 g) in 150 mL of anhydrous pyridine was cooled to 0° C. (ice bath). Para-toluenesulfonyl chloride (4.7 g) was added to the solution in one portion and the cooled mixture was left to stir for 7 hours. The reaction was quenched by adding 50 mL of ice water and removing all volatiles under reduced pressure. The product, N-t-butoxycarbonyl-L-tryptophan-(N'-(7-(4'-methylphen-1-yl)sulfonyloxy)heptyl)amide was isolated by column chromatography on silica gel using 10–40% ethyl acetate/hexane as eluant. This material crystallized on standing, MS: 572 (MH$^+$).

C. Alternatively, to a solution of N-t-butoxycarbonyl-L-tryptophan (5.0 g, 16.45 mmol), 6-amino-1-hexanol (2.31 g, 19.74 mmol) and 1-hydroxybenzotriazoleH$_2$O (2.52 g, 16.45 mmol) in dry DMF (50 mL) at room temperature under argon was added EDCI (4.73 g, 24.68 mmol). After stirring overnight, the DMF was removed under high vacuum. The residue was partitioned between ethyl acetate (150 mL) and 1N HCl (75 mL). The organic layer was further washed with 1N HCl (75 mL), saturated sodium bicarbonate solution (2×75 mL), and finally with brine (50 mL). The organic layer was dried (MgSO$_4$) and evaporated to dryness to yield 6.45 g (97%) N-t-butoxycarbonyl-L-tryptophan-N'-(6-hydroxyhexyl)amide as a white foam, MS: 404.3 (M+H)$^+$. The purity of the product was confirmed by analytical HPLC.

D. Proceeding further, to N-t-butoxycarbonyl-L-tryptophan-N'-(6-hydroxyhexyl)amide (5.5 g, 13.64 mmol) in 150 mL dry pyridine at 0° C. under argon was added 3.9 g (20.46 mmol) p-toluenesulfonyl chloride. The homogeneous solution was stirred at the same temperature overnight. The reaction was quenched with 25 mL of water and excess pyridine was removed under reduced pressure. The residue was dissolved in ethyl acetate (120 mL) and washed with 1N HCl (2×50 mL), saturated NaHCO$_3$ solution (50 mL), and brine (50 mL). The organic layer was dried (MgSO$_4$) and evaporated to give as a pale yellow oil, N-t-butoxycarbonyl-L-tryptophan-(N'-(6-(4'-methylphen-1-yl)sulfonyloxy)hexyl)amide (5.77 g, 76%), MS: 558.3 (M+H)$^+$.

E. To 5-hydroxytryptophan (3.5 g, available from Sigma) and triethylamine (5.6 mL) in water (25 mL) and tetrahydrofuran (50 mL) was added BOC-ON (2-(t-butoxycarbonyloxyimino)-2-phenylacetonitrile). After 2.5 hours, the tetrahydrofuran was removed, 10% Na$_2$CO$_3$ (20 mL) was added and the mixture was partitioned with ether (50 mL). The aqueous portion was further extracted with ether (20 mL) and then acidified with cold 10% HCl in a two-phase system containing ethyl acetate (100 mL). The ethyl acetate portion was separated and washed with water (30 mL), brine, dried over anhydrous MgSO$_4$ and concentrated to give a syrup. The syrup was reacted with 6-amino-1-hexanol in a similar manner as described above in Example 1C to yield N-t-butoxycarbonyl-L-(5-hydroxy)tryptophan-N'-(6- hydroxyhexyl)amide. Half of this product was taken up in 40 mL of DMF and treated with K2CO$_3$ (5 g) and iodomethane (1.2 g) at room temperature overnight. The reaction mixture was then partitioned between water (50 mL) and ethyl acetate (80 mL), the organic portion was further washed with water (2×20 mL), brine, dried over anhydrous MgSO$_4$ and concentrated to an oil. Purification of the product, N-t-butoxycarbonyl-L-(5-methoxy)tryptophan-N'-(6-hydroxyhexyl)amide, was then done by silica gel chromatography; $^1$H NMR: δ (CDCl$_3$) 0.9–1.6 (m, CH$_2$, 8H); 1.45 (s, 9H); 2.7–3.3 (m, 5H); 3.6 (t, 2H); 3.85 (s, 3H); 4.35 (m, 1H); 5.3 (broad d, 1H); 5.85 (broad t, 1H); 6.75–8.3 (m, 4H); 8.73 (broad s, 1H).

F. In a similar manner, the following compounds are made:

N-t-butoxycarbonyl-L-(5-ethoxy)tryptophan-N'-(6-hydroxyhexyl)amide;

N-t-butoxycarbonyl-L-(5-propoxy)tryptophan-N'-(6-hydroxyhexyl)amide;

N-t-butoxycarbonyl-L-(S-ethyl)tryptophan-N'-(6-hydroxy-hexyl)amide; and

N-t-butoxycarbonyl-L-(4-methyl)tryptophan-N'-(6-hydroxyhexyl)amide.

EXAMPLE 3

Compounds of Formula (H)

A. N-t-Butoxycarbonyl-L-tryptophan-(N'-(4'-methylphen-1-yl)sulfonyloxyheptyl)amide (6.78 g) was added portion-wise to a solution of NaH (60% in oil, 1.9 g) in 1.1 liters of anhydrous tetrahydrofuran and left to stir overnight. The reaction mixture was concentrated and taken up in water (150 mL) and $CH_2Cl_2$ (150 mL). The aqueous phase was made slightly acidic with 2.5% HCl (pH=3–4) and the organic phase was isolated (3×150 mL) and washed consecutively with cold 2.5% HCl (150 mL), 5% $NaHCO_3$ (150 mL) and brine (150 mL). The organic phase was dried ($MgSO^4$), filtered and concentrated providing a green-yellow semi-solid material. Purification by chromatography on silica gel gave (11S)-11-N'-(t-butoxycarbonyl)amino-10-oxo-1,9-diaza-tricyclo[11.6.1.0$^{14,19}$]eicosa-13(20),14(19),15,17-tetraene, m.p. 208–209° C., MS: 400 (M+H)$^+$.

B. Alternatively, to N-t-butoxycarbonyl-L-tryptophan-(N'-(6-(4'-methylphen-1-yl)sulfonyloxy)hexyl)amide (5 g, 8.97 mmol) in one liter of dry THF at 0° C. under argon was added 4 equivalents of 60% NaH (1.44 g, 36 mmol) in small portions over 10 minutes. The mixture was then stirred at room temperature overnight. The resulting yellow mixture was evaporated down to ~200 mL and 1 liter of distilled water was added. The mixture was then acidified with 1N HCl with vigorously stirring. The yellow precipitate was collected by filtration and dried over $P_2O_5$ at high vacuum overnight. The dry crude product (8 g) was chromatographed on silica-gel 60, eluted with 30% ethyl acetate in $CH_2Cl_2$ to give 1.2 g (35%) of (10S)-10-N'-(t-butoxycarbonyl)amino-9-oxo-1,8-diaza-tricyclo[10.6.1.0$^{13,18}$]nonadeca-12(19),13(18),14,16-tetraene as a white powder, MS: 386 (M+H)+, m.p. 222–223° C.

C. Alternatively, to a solution of the N-t-butoxycarbonyl-L-tryptophan-(N'-(6-(4'-methylphen-1-yl)sulfonyloxy) hexyl)amide (1.21 g, 2.17 mmol) in 45 ml reagent grade methylene chloride were added 15 ml of 40% aqueous KOH and 0.3 equivalent of benzyl triethyl ammonium chloride (0.65 mmol, 148 mg). The two phase mixture was stirred vigorously at room temperature overnight. The organic layer was separated and the aqueous layer was extracted with 25 mL methylene chloride. The combined organic layer was washed with water (25 mL), dried ($MgSO_4$), and evaporated to dryness. The residue was stirred in 10% ether in pet ether at 0° C. for 15 minutes and filtered to give 792 mg (93%) of (10S)-10-N'-(t-butoxy-carbonyl)amino-(9-oxo-1,8-diaza-tricyclo[10.6.1.0$^{13,18}$]nonadeca-12(19),13(18),14,16-tetraene as a white powder.

EXAMPLE 4

Compounds of Formula (J)

A. (11S)-11-N'-(t-Butoxycarbonyl)amino-(10-oxo-1,9-diaza-tricyclo[11.6.1.0$^{14,19}$]eicosa-13(20),14(19),15,17-tetraene (850 mg) was dissolved in 5 mL of a 10% trifluoroacetic acid in methylene chloride solution and stirred for 1 hour. The volatiles were removed under reduced pressure. The residue was taken up in $CH_2Cl_2$ (40 mL) and 1N NaOH (40 mL) and transferred to a separatory funnel. The organic phase was isolated and washed with brine, dried ($MgSO_4$), filtered and concentrated to obtain 654 mg of (11S)-11-amino-(10-oxo-1,9-diazatricyclo[11.6.1.0$^{14,19}$]eicosa-13(20),14(19),15,17-tetraene.

B. Alternatively, (10S)-10-N'-(t-butoxycarbonyl)amino-(9-oxo-1,8-diazatricyclo[10.6.1.0$^{14,19}$]nonadeca-12(19),13(18),14,16-tetraene (0.5 mmol, 193 mg) was stirred in 20% TFA/$CH_2Cl_2$ (10 mL) at room temperature for 2 hours. Excess of TFA and solvent was removed under reduced pressure. The residue was dissolved in ethyl acetate (30 mL) and washed with 1N HCl (25 mL), brine (10 mL), and dried ($MgSO_4$). Evaporation to dryness gave 140 mg (quant.) of (10S)-10-amino-(9-oxo-1,8-diazatricyclo[10.6.1.0$^{13,18}$]-nonadeca-12(19),13(18),14,16-tetraene as a white foam, m.p. 157–160° C., MS: 286.2 (M+H)$^+$.

EXAMPLE 5

Compounds of Formula (Ia)

A. To a stirred solution of (11S)-11-amino-(10-oxo-1,9-diaza-tricyclo[11.6.1.0$^{14,19}$]eicosa-13(20),14(19),15,17-tetraene (654 mg) and racemic 4-methyl-2-t-butoxycarbonylmethylpentanoic acid (800 mg) in 30 mL of anhydrous DMF under argon was added 1-hydroxybenzotriazole (360 mg), followed by EDCI (940 mg). The mixture was left to stir overnight and then the DMF was removed under reduced pressure. The residue was taken up in a mixture of $CH_2Cl_2$ (100 mL) and 1.5% cold HCl (100 mL) and transferred to a separatory funnel. The organic phase was isolated and washed consecutively with 1.5% HCl (100 mL), 5% $NaHCO_3$ (100 mL) and brine (100 mL). The $CH_2Cl_2$ phase was dried ($MgSO_4$), filtered and concentrated providing a semi-crystalline product, (11S)-5-methyl-3-(10-oxo-1,9-diazatricyclo-[11.6.1.0$^{14,19}$]eicosa-13 (20),14(19),15,17-tetraen-11-ylcarbamoyl)hexanoic acid t-butyl ester. The two individual stereoisomers of this compound were separated by chromatography on silica gel with ethyl acetate/hexane as eluant. The less polar stereoisomer had a melting point of 154–157° C., $[\alpha]_D^{24}$=–43.9°, c=23.8 mg/2 mL $CHCl_3$, while the more polar stereoisomer had a melting point of 168–171° C., $[\alpha]_D^{24}$=–19.1°, c=11.86 mg/2 mL $CHCl_3$.

B. Alternatively, to a solution of (2R)-4-methyl-2-(t-butoxycarbonylmethyl)pentanoic acid as prepared above (2.39 g, 10.4 mmol), HOBt-$H_2O$ (2.5 g, 1 eq.), N-methylmorpholine (2.3 mL, 2 eq.), and (10S)-10-amino-(9-oxo-1,8-diazatricyclo[10.6.1.0$^{13,18}$]nonadeca-12(19), 13(18),14,16-tetraene (2.96 g, 1 eq.) in dry DMF (200 mL) under argon was added EDCI (3.96 g, 2.0 eq.). The resulting mixture was stirred overnight, then the next morning the DMF was removed at 35° C. under high vacuum. The residue was partitioned between $CH_2Cl_2$ (150 mL)/water (75 mL), then the organic layer was washed with 0.5N HCl (2×75 mL), saturated $NaHCO_3$ (2×75 mL) and finally with brine (1×75 mL). After drying the $CH_2Cl_2$ layer over $Na_2SO_4$, it was filtered and evaporated to dryness. Purification by column chromatography (petroleum ether to 30% ethyl acetate/petroleum ether) gave (3R,10S)-5-methyl-3-(9-oxo-1,8-diaza-tricyclo[10.6.1.0$^{13,18}$]nonadeca-12(19),13 (18),14,16-tetraen-10-ylcarbamoyl)hexanoic acid t-butyl ester (3.24 g, 62.7%).

C. In a similar manner, the following compounds of formula (Ia) were prepared:

(3R,10S)-4-phenyl-3-(9-oxo-1,8-diaza-tricyclo[10.6.1.0$^{13,18}$]-nonadeca-12(19),13(18),14,16-tetraen-10-ylcarbamoyl)butanoic acid t-butyl ester, MS: 532 (M+H)$^+$;

(3R,10S)-4-cyclohexyl-3-(9-oxo-1,8-diazatricyclo[10.6.1.0$^{13,18}$]-nonadeca-12(19),13(18),14,16-tetraen-10-ylcarbamoyl)butanoic acid t-butyl ester, MS: 538 (M+H)$^+$;

(3R,10S)-6-phenyl-3-(9-oxo-1,8-diaza-tricyclo[10.6.1.0$^{13,18}$]-nonadeca-12(19),13(18),14,16-tetraen-10-ylcarbamoyl)hexanoic acid t-butyl ester, MS: 560 (M+H)$^+$; and (3R,10S)-3-(9-oxo-1,8-diaza-tricyclo[10.6.1.0$^{13,18}$]nonadeca-12(19),13(18),14,16-tetraen-10-ylcarbamoyl)hexanoic acid t-butyl ester, MS: 484 (M+H)$^+$;

(3R,10S)-2-methoxycarbonyl-5-methyl-3-(9-oxo-1,8-diazatricyclo[10.6.1.0$^{13,18}$]nonadeca-12(19),13(18),14,16-tetraen-10-ylcarbamoyl)hexanoic acid benzyl ester, MS: 590 (M+H)$^+$;

(3R,10S)-4-cyclopentyl-3-(9-oxo-1,8-diazatricyclo[10.6.1.0$^{13,18}$]nonadeca-12(19),13(18),14,16-tetraen-10-ylcarbamoyl)butanoic acid t-butyl ester;

(3R,10S)-4-cyclopentyl-3-(9-oxo-1,8-diazatricyclo[10.6.1.0$^{13,18}$]nonadeca-12(19),13(18),14,16-tetraen-10-ylcarbamoyl)butanoic acid methyl ester; MS: 496 (M+H)$^+$;

(3R,10S)-4-cyclopropyl-3-(9-oxo-1,8-diazatricyclo[10.6.1.0$^{13,18}$]nonadeca-12(19),13(18),14,16-tetraen-10-ylcarbamoyl)butanoic acid t-butyl ester;

Similarly, the following compound was prepared:

(3RS,10S)-N-benzyloxy-N-formyl-5-methyl-3-(9-oxo-1,8-diaza-tricyclo[10.6.1.0$^{13,18}$]nonadeca-12(19),13(18),14,16-tetraen-10-ylcarbamoyl)hexylamine.

D. Alternatively, to (2R)-4-methyl-2-(t-butoxy-carbonylmethyl)pentanoic acid (1g, 4.34 mmol) in dry THF (100 mL) at −78° C. under argon was added NaN(TMS)$_2$ (1.0M in THF, 10.9 mL, 2.5 eq) dropwise and the mixture was stirred for 1 hour. Iodomethane (0.33 mL, 1.2 eq) was added and the resulting mixture was stirred overnight from −78° C. to room temperature. The next day the reaction was quenched with water (100 mL). After extracting with ether (3×100 mL), the aqueous layer was combined with ethyl acetate and with stirring was added 4N HCl to pH=2. Sodium chloride was also added to saturation and the aqueous layer was extracted with ethyl acetate (3×100 mL). The combined organic extracts were dried over Na$_2$SO$_4$, filtered and concentrated to give (2R)-4-methyl-2-((1-methyl-1-t-butoxy-carbonyl)methyl)pentanoic acid as a dark brown oil (1 g). To this crude reaction product (500 mg) and (10S)-10-amino-(9-oxo-1,8-diaza-tricyclo[10.6.1.0$^{13,18}$]nonadeca-12(19),13(18),14,16-tetraene (399 mg, 0.7 eq) in dry DMF at 0° C. under argon was added HOBt-H$_2$O (1.1 eq, 234 mg), followed by EDCI (663 mg, 2.5 eq). The resulting mixture was stirred overnight from 0° C. to room temperature. Most of the DMF was removed by pump distillation at 65° C. Then, the residue was partitioned between CH$_2$Cl$_2$ (150 mL). After washing with 0.5N HCl (2×75 mL), saturated NaHCO$_3$ (2×75 mL) and brine (1×75 mL), the organic layer was dried over Na$_2$SO$_4$, filtered and evaporated to dryness. The crude material was purified by flash column chromatography on silica eluting with 30% ethyl acetate in petroleum ether to yield a mixture of three compounds, the two individual stereoisomers of (3R,10S)-2-methyl-5-methyl-3-(9-oxo-1,8-diaza-tricyclo-[10.6.1.0$^{13,18}$]nonadeca-12(19),13(18), 14,16-tetraen-10-ylcarbamoyl) hexanoic acid t-butyl ester and (3R,10S)-5-methyl-3-(9-oxo-1,8-diaza-tricyclo-[10.6.1.0$^{13,18}$]nonadeca-12(19), 13(18), 14,16-tetraen-10-ylcarbamoyl)hexanoic acid t-butyl ester. Further purification provided separation of the three compounds; (3R,10S)-5-methyl-3-(9-oxo-1,8-diazatricyclo-[10.6.1.0$^{13,18}$]nonadeca-12(19),13(18),14,16-tetraen-10-ylcarbamoyl)hexanoic acid t-butyl ester (13 mg) as a white solid; 1:1 mixture of the stereoisomers (5 mg) as a white solid; and the less polar stereoisomer of (3R,10S)-2-methyl-5-methyl-3-(9-oxo-1,8-diaza-tricyclo-[10.6.1.0$^{13,18}$]nonadeca-12(19),13(18),14,16-tetraen-10-ylcarbamoyl)hexanoic acid t-butyl ester (15 mg); 300 MHz $^1$H NMR in CDCL$_3$ (less polar diastereomer): δ (−0.2)–(−0.05) (m, 1H); 0.5–0.7 (m, 1H); 0.9 (dd, J=4 Hz, J=6.7 Hz, 6H); 1.15 (d, J=8.4 Hz, 3H); 1.18–1.4 (m, 3H); 1.41 (s, 9H); 1.45–1.73 (m, 4H); 1.75–1.8 (m, 2H); 2.5–2.7 (m, 3H); 2.89 (dd, J=10.9 Hz J=15 Hz, 1H); 3.34–3.5 (m, 2H); 3.95–4.1 (m, 1H); 4.25–4.4 (m, 1H); 4.72–4.82 (m, 1H); 5.22–5.3 (m, 1H); 6.52 (d, J=7.5 Hz, 1H); 6.91 (s, 1H); 7.13 (dd, J=6.7 Hz, J=8.4 Hz, 1H); 7.22 (dd, J=5 Hz, J=7.1 Hz, 1H); 7.34 (d, J=8.4 Hz, 1H); 7.84 (d, J=8.4 Hz, 1H).

EXAMPLE 6

Compounds of Formula (Ib)

A. The less polar stereoisomer of (11S)-5-methyl-3-(10-oxo-1,9-diazatricyclo[11.6.1.0$^{14,19}$]eicosa-13(20),14(19),15,17-tetraen-11-yl-carbamoyl)hexanoic acid t-butyl ester (300 mg) was covered with 5 mL of a 10% trifluoroacetic acid/methylene chloride solution and left to stir. After 2.5 hours, TLC indicated that the reaction was complete. All volatiles were removed under reduced pressure. The residue was taken up in CH$_2$Cl$_2$ (40 mL) and transferred to separatory funnel and washed consecutively with 0.5% HCl (40 mL) and brine (40 mL). The organic phase was dried (MgSO$_4$), filtered and concentrated to provide the less polar stereoisomer of (11S)-5-methyl-3-(10-oxo-1,9-diazatricyclo[11.6.1.0$^{14,19}$]eicosa-13(20),14(19),15,17-tetraen-11-ylcarbamoyl)hexanoic acid.

B. In a similar manner, the more polar stereoisomer of (11S)-5-methyl-3-(10-oxo-1,9-diazatricyclo[11.6.1.0$^{14,19}$]eicosa-13(20),14(19),15,17-tetraen-11-ylcarbamoyl)hexanoic acid t-butyl ester was hydrolyzed to yield the more polar stereoisomer of (11S)-5-methyl-3-(10-oxo-1,9-diazatricyclo-[11.6.1.0$^{14,19}$]eicosa-13(20),14(19),15,17-tetraen-11-ylcarbamoyl)hexanoic acid.

C. Alternatively, (3R,10S)-5-methyl-3-(9-oxo-1,8-diazatricyclo-[10.6.1.0$^{13,18}$]nonadeca-12(19),13(18),14,16-tetraen-10-ylcarbamoyl)hexanoic acid t-butyl ester (3.24 g, 6.5 mmol) was taken up in 95% TFA (aqueous) (30 mL) at 0° C. and then stirred for 20 minutes. The ice bath was then removed and the mixture was stirred for another 1 hour. After concentrating it to an oil, the residue was taken up in ethyl acetate (250 mL) and washed with water (7×150 mL). The organic layer was dried over Na$_2$SO4, filtered and evaporated to dryness to yield a single stereoisomer of (3R,10S)-5-methyl-3-(9-oxo-1,8-diaza-tricyclo[10.6.1.0$^{13,18}$]nonadeca-12(19),13(18),14,16-tetraen-10-ylcarbamoyl)hexanoic acid as a white powder, 2.83 g (98.4% yield); MS: 442 (M+H)$^+$ D. In a similar manner, but replacing (3R,10S)-5-methyl-3-(9-oxo-1,8-diazatricyclo[10.6.1.0$^{13,18}$]nonadeca-12(19), 13(18),14,16-tetraen-10-ylcarbamoyl)hexanoic acid t-butyl ester with the appropriate compound of formula (Ia), the following compounds of formula (Ib) were prepared:

(3R,10S)-4-phenyl-3-(9-oxo-1,8-diazatricyclo[10.6.1.0$^{13,18}$]-nonadeca-12(19),13(18),14,16-tetraen-10-ylcarbamoyl)butanoic acid, MS: 474 (M−H)$^+$;

(3R,10S)-4-cyclohexyl-3-(9-oxo-1,8-diazatricyclo[10.6.1.0$^{13,18}$]-nonadeca-12(19),13(18),14,16-tetraen-10-ylcarbamoyl)butanoic acid, MS: 482 (M+H)$^+$;

(3R,10S)-3-cyclohexyl-3-(9-oxo-1,8-diazatricyclo[10.6.1.0$^{13,18}$]-nonadeca-12(19),13(18),14,16-tetraen-10-ylcarbamoyl) propanoic acid, MS: 468 (M+H)$^+$;

(3R,10S)-6-phenyl-3-(9-oxo-1,8-diazatricyclo[10.6.1.0$^{13,18}$] nonadeca-12(19),13(18),14,16-tetraen-10-ylcarbamoyl)hexanoic acid, MS: 502 (M–H)$^-$;

(3R,10S)-3-(9-oxo-1,8-diaza-tricyclo[10.6.1.0$^{13,18}$] nonadeca-12(19),13(18),14,16-tetraen-10-ylcarbamoyl) hexanoic acid, MS: 426 (M–H)$^-$;

(3R,10S)-2-amino-5-methyl-3-(9-oxo-1,8-diazatricyclo[10.6.1.0$^{13,18}$]nonadeca-12(19),13(18),14,16-tetraen-10-ylcarbamoyl)hexanoic acid, MS: 457 (M+H)$^+$;

(3R,10S)-2-hydroxy-5-methyl-3-(9-oxo-1,8-diazatricyclo[10.6.1.0$^{13,18}$]nonadeca-12(19),13(18),14,16-tetraen-10-ylcarbamoyl)hexanoic acid, MS: 458 (M+H)$^+$;

(3R,9S)-5-methyl-3-(8-oxo-1,7-diazatricyclo[9.6.1.0$^{12,17}$] octadeca-11(18),12(17),13,15-tetraen-9-ylcarbamoyl) hexanoic acid;

(3R,10S)-4-cyclopentyl-3-(9-oxo-1,8-diazatricyclo[10.6.1.0$^{13,18}$]nonadeca-12(19),13(18),14,16-tetraen-10-ylcarbamoyl)butanoic acid; MS: 509;

(3R,10S)-3-cyclopentyl-3-(9-oxo-1,8-diazatricyclo[10.6.1.0$^{13,18}$]nonadeca-12(19),13(18),14,16-tetraen-10-ylcarbamoyl)propionic acid; MS: 454;

(3R, 10S)-3-cyclopropyl-3-(9-oxo-1,8-diazatricyclo[10.6.1.0$^{13,18}$]nonadeca-12(19),13(18),14,16-tetraen-10-ylcarbamoyl)butanoic acid; MS: 439;

(3R,10S)-6-(biphenyl-4-yl)-3-(9-oxo-1,8-diazatricyclo-[10.6.1.0$^{13,18}$]-nonadeca-2(19),13(18),14,16-tetraen-10-ylcarbamoyl)hexanoic acid; MS: 579; and (3R,10S)-3-(9-oxo-1,8-diazatricyclo[10.6.1.0$^{13,18}$] nonadeca-12(19),13(18),14,16-tetraen-10-ylcarbamoyl)-5-(thiophen-2-yl)pentanoic acid, MS: 496.3 (M+H)$^+$.

Similarly prepared is:

(3R,9S)-4-cyclopentyl-3-(8-oxo-1,7-diazatricyclo[9.6.1.0$^{12,17}$]octadeca-11(18),12(17),13,15-tetraen-9-ylcarbamoyl)butanoic acid;

E. (3R,10S)-5-Methyl-3-(9-oxo-1,8-diazatricyclo[10.6.1.0$^{13,18}$]-nonadeca-12(19),13(18),14,16-tetraen-10-ylcarbamoyl)hexanoic acid (183 mg) was taken up in 40 mL of dry CH$_2$Cl$_2$ and at 0° C. ethanol (0.5 mL, 5 eq) was added followed by N,N-dimethylaminopyridine (0.1 eq, 5 mg) and finally EDCI (209 mg, 5 eq). The resulting solution was stirred from 0° C. to room temperature overnight. Additional CH$_2$Cl$_2$ (100 mL) was added and the mixture was washed with 0.5N HCl (2×50 mL), saturated NaHCO$_3$ (2×50 mL) and finally with brine (1×50 mL). The organic layer was dried over Na$_2$SO$_4$, filtered and evaporated to dryness. Recrystallization from ethyl acetate and petroleum ether gave (3R,10S)-5-Methyl-3-(9-oxo-1,8-diaza-tricyclo[10.6.1.0$^{13,18}$]nonadeca-12(19),13(18),14,16-tetraen-10-ylcarbamoyl)hexanoic acid ethyl ester as a white solid (Yield: 108 mg, 55%), MS: 470 (M+H)$^+$.

Similarly prepared was (3R,10S)-4-cyclopentyl-3-(9-oxo-1,8-diazatricyclo[10.6.1.0$^{13,18}$]nonadeca-12(19),13(18),14,16-tetraen-10-ylcarbamoyl)butanoic acid ethyl ester; MS: 496 (M+H)$^+$;

F. Alternatively, the less polar stereoisomer of (3R,10S)-2-methyl-5-methyl-3-(9-oxo-1,8-diazatricyclo-[10.6.1.0$^{13,18}$]nonadeca- 12(19),13(18),14,16-tetraen-10-ylcarbamoyl)hexanoic acid t-butyl ester prepared in Example 5D above (15 mg) was taken up in CH$_2$Cl$_2$ (2.4 mL) and TFA (0.6 mL) and the resulting mixture was stirred at room temperature for 4 hrs. The solvent was removed under reduced pressure at 35° C. Then ethyl acetate was added and the solution was washed with water (3×10 mL). The organic layer was dried over Na$_2$SO$_4$, filtered and evaporated to dryness. Recrystallization from ethyl acetate/petroleum ether gave (3R,10S)-2-methyl-5-methyl-3-(9-oxo-1,8-diazatricyclo[10.6.1.0$^{13,18}$]nonadeca-12(19),13(18),14,16-tetraen-10-ylcarbamoyl)hexanoic acid as a white solid (7 mg), MS: 456.3 (M+H)$^+$.

G. In a similar manner, the 1:1 mixture of stereoisomers of (3R,10S)-2-methyl-5-methyl-3-(9-oxo-1,8-diazatricyclo[10.6.1.0$^{13,18}$]-nonadeca-12(19),13(18),14,16-tetraen-10-ylcarbamoyl)hexanoic acid t-butyl ester (prepared in Example 5D above) (5 mg) was hydrolyzed to yield 3 mg of a white solid; 300 MHz $^1$H NMR in CDCl$_3$: δ (–0.5)–(–0.3) (m, 1H); 0.6–0.8 (m, 1H); 0.8–1.05 (m, 6H); 1.05–1.22 (m, 2H); 1.35 (3H, dd, J=9 Hz); 1.4–1.7 (m, 3H); 1.7–1.95 (m, 3H); 2.3–2.48 (m, 1H); 2.54–2.73 (m, 1H); 2.8–3.0 (m, 2H); 3.38–3.5 (m, 1H); 3.52–3.72 (m, 1H); 3.8–3.98 (m, 1H); 4.34–4.45 (m, 1H); 4.7–4.84 (m, 1H); 5.0–5.08 (m, 1H); 6.8 (d, 1H); 7.15–7.25 (m, 1H); 7.25–7.32 (m, 1H); 7.35 (d, J=8.4 Hz, 1H); 7.88 (d, J=8.4 Hz).

H. Alternatively, (3R,10S)-2-methoxycarbonyl-5-methyl-3-(9-oxo-1,8-diazatricyclo[10.6.1.0$^{13,18}$]nonadeca-12(19),13(18),14,16-tetraen-10-ylcarbamoyl)hexanoic acid benzyl ester was taken up in ethanol (35 mL, some heating was required) and ammonium formate 1642 mg, 3 eq) was added followed by 10% Pd on activated charcoal (100 mg). After stirring under argon at room temperature for 3 hrs. the reaction was complete. The mixture was suction-filtered through a 1 cm bed of celite, then it was concentrated, MeOH was added and it was filtered through a plug of cotton. After concentrating, CH$_2$Cl$_2$ was added to the residue and it was stirred vigorously and then filtered. The filtrate was concentrated and recrystallized from ethyl acetate/pet. ether to give (3R,10S)-2-methoxycarbonyl-5-methyl-3-(9-oxo-1,8-diazatricyclo[10.6.1.0$^{13,18}$]nonadeca-12(19),13(18),14,16-tetraen-10-ylcarbamoyl)hexanoic acid as a white solid (yield: 140 mg), MS: 500.3 (M+H)$^+$.

I. (3R,10S)-2-Methoxycarbonyl-5-methyl-3-(9-oxo-1,8-diaza-tricyclo[10.6.1.0$^{13,18}$]nonadeca-12(19),13(18),14,16-tetraen-10-ylcarbamoyl) hexanoic acid was taken up in ethanol (25 mL) and then 1 N LiOH (0.3 mL, 3 eq) was added dropwise. The resulting homogeneous solution was stirred at room temperature for 3 hrs. Most of the ethanol was removed under reduced pressure at 30° C. Then water (5 mL) and ethyl acetate (30 mL) was added and with stirring, 4 N HCl was added until pH=2. The ethyl acetate layer was further washed with brine, dried over Na$_2$SO$_4$, filtered and evaporated to dryness. Purified by reverse phase HPLC to give 47 mg of (3R,10S)-2-carboxy-5-methyl-3-(9-oxo-1,8-diazatricyclo[10.6.1.0$^{13,18}$]nonadeca-12(19), 13(18),14,16-tetraen-10-ylcarbamoyl)hexanoic acid, as a white solid, MS: 484.5 (M–H)$^-$.

EXAMPLE 7

Compounds of Formula (Ic)

A. A solution of the less polar stereoisomer of (11S)-5-methyl-3-(10-oxo-1,9-diazatricyclo[11.6.1.0$^{14,19}$]eicasa-13 (20),14(19), 15,17-tetraen-11-ylcarbamoyl)hexanoic acid (210 mg) and 5-hydroxybenzotriazole monohydrate (109 mg) in anhydrous DMF (20 mL) under argon was cooled to 0° C. (ice bath). To this mixture was added EDCI (282 mg) and stirring was continued for 0.5 hours. O-benzylhydroxylamine (0.27 mL) was added to the solution and the reaction mixture was left to warm to room temperature overnight. All volatiles were removed under reduced pressure. The residue was taken up in $CH_2Cl_2$ (100 mL) and 20% HCl (100 mL) and transferred to a separatory funnel. The organic phase was isolated and the aqueous phase washed (2×100 mL) with $CH_2Cl_2$. The organic materials were then washed consecutively with 5% $NaHCO_3$, brine, dried ($MgSO_4$), filtered and concentrated to provide (11S)-N-benzyloxy-5-methyl-3-(10-oxo-1,9-diaza-tricyclo[11.6.1.0$^{14,19}$]eicosa-13(20),14(19),15,17-tetraen-11-ylcarbamoyl) hexanamide as a crystalline product. The product was further purified by column chromatography on silica gel followed by crystallization from hot ethyl acetate/$CH_2Cl_2$, to provide the more polar stereoisomer of the compound having a melting point at 232–233° C. m.p., and the less polar stereoisomer of the compound having a melting point at 251–253° C.

B. Alternatively, to a solution of (3R,10S)-5-methyl-3-(9-oxo-1,8-diazatricyclo[10.6.1.0$^{13,18}$]nonadeca-12(19),13(18),14,16-tetraen-10-ylcarbamoyl)hexanoic acid (2.5 g, 5.82 mmol), $HOBtH_2O$(0.89 g, 1 eq.) and O-benzyl hydroxylamine (2.2 mL, 3 eq.) in DMF (200 mL) at 0° C. was added EDCI (2.77 g, 2.5 eq.). The resulting mixture was then stirred overnight. DHF was removed by pump distillation at 65° C. To the residue was then added methanol (14 mL) followed by ether (140 mL). With stirring at 0° C., 0.5 N HCl (140 mL) was added, followed by petroleum ether (140 mL). The mixture was stirred at 0° C. for 15 minutes, then the white solid was suction filtered and subsequently washed with water (100 mL) followed by 1:1 ether/petroleum ether (100 mL). Drying under vacuum ($P_2O_5$) for 3 hours gave (3R,10S)-N-benzyloxy-5-methyl-3-(9-oxo-1,8-diazatricyclo[10.6.1.0 $^{13,18}$]-nonadeca-12(19),13(18),14,16-tetraen-10-ylcarbamoyl)hexanamide as a white solid (2.7 g, 84.9%).

C. In a similar manner, but replacing (3R,10S)-5-methyl-3-(9-oxo-1,8-diazatricyclo[10.6.1.0$^{13,18}$]nonadeca-12(19),13(18),14,16-tetraen-10-ylcarbamoyl)hexanoic acid with the appropriately substituted compound of formula (Ib) the following compounds of formula (Ic) were prepared:

(3R,10S)-N-benzyloxy-2-methoxycarbonyl-5-methyl-3-(9-oxo-1,8-diaza-tricyclo[10.6.1.0$^{13,18}$]nonadeca-12(19),13(18),14,16-tetraen-10-ylcarbamoyl)hexanamide, MS: 605.3 (M+H)$^+$;

(3R,10S)-N-benzyloxy-6-phenyl-3-(9-oxo-1,8-diazatricyclo[10.6.1.0$^{13,18}$]nonadeca-12(19),13(18),14,16-tetraen-10-ylcarbamoyl)hexanamide, MS: 609 (M+H)$^+$;

(3R,10S)-N-benzyloxy-3-(9-oxo-1,8-diazatricyclo[10.6.1.0$^{13,18}$]nonadeca-12(19),13(18),14,16-tetraen-10-ylcarbamoyl)hexanamide, MS: 533 (M+H)$^+$.

D. In a similar manner, but replacing O-benzyl hydroxylamine with 2-dimethylaminoethylamine or 1-methyl-4-hydroxypiperidine, the following derivatives of formula (I) were prepared:

(3R,10S)-5-methyl-3-(9-oxo-1,8-diazatricyclo[10.6.1.0$^{13,18}$]nonadeca-12(19),13(18),14,16- tetraen-10-ylcarbamoyl)hexanoic acid 1-(2-dimethylaminoethyl) amide, MS: 512.49 (M+H)$^+$;

(3R,10S)-5-methyl-3-(9-oxo-1,8-diazatricyclo[10.6.1.0$^{13,18}$]nonadeca-12(19),13(18),14,16- tetraen-10-ylcarbamoyl)hexanoic acid 1-methylpiperidin-4-yl ester, MS: 539.51 (M+H)$^+$;

EXAMPLE 8

Compounds of Formula (Id)

A. To a solution of the more polar stereoisomer of (11S)-N-benzyloxy-5-methyl-3-(10-oxo-1,9-diazatricyclo-[11.6.1.0$^{14,19}$]eicosa-13(20),14(19),15,17-tetraen-11-ylcarbamoyl)hexanamide (90 mg) in ethanol/tetrahydrofuran (350 mL; 2:1) was added 10% palladium on charcoal (30 mg). The material was stirred with a constant stream of hydrogen gas bubbling through it. After 3 hours TLC (10% $CH_3OH/CH_2Cl_2$) showed the reaction was complete. The material was filtered through a bed of celite (3X) and concentrated under reduced pressure to an almost dry residue. Methylene chloride (15 mL) was added and the material was again concentrated under reduced pressure until almost dried and then repeated. To the residue was added 3–4 drops of methanol followed by methylene chloride (15 mL). The material was stirred with cooling (ice bath) and ether (5 mL) and then hexane (2 mL) was added. A crystalline material slowly emerged and was collected by filtration to yield 50 mg of the more polar stereoisomer of (11S)-N-hydroxy-5-methyl-3-(10-oxo-1,9-diazatricyclo-[11.6.1.0$^{14,19}$]eicosa-13(20),14(19),15,17-tetraen-11-ylcarbamoyl)hexanamide, m.p. 197–201° C., $[\alpha]_D^{23}$=−85.1° (3.5 mg/1.0 mL DMSO).

B. In a similar manner, but replacing the more polar stereoisomer of (11S)-N-benzyloxy-5-methyl-3-(10-oxo-1,9-diazatricyclo-[11.6.1.0$^{14,19}$]-eicosa-13(20),14(19),15,17-tetraen-11-ylcarbamoyl)hexanamide with the less polar, the less polar stereoisomer of (11S)-N-hydroxy-5-methyl-3-(10-oxo-1,9-diazatricyclo[11.6.1.0$^{14,19}$]eicosa-13(20),14(19), 15,17-tetraen-11-ylcarbamoyl)hexanamide was made, m.p. 212–216° C., $[\alpha]_D^{23}$=−38.5° (4.7 mg/1.0 mL $CH_3OH$).

C. Alternatively, (3R,10S)-N-benzyloxy-5-methyl-3-(9-oxo-1,8-diazatricyclo[10.6. 1.0$^{13,18}$]nonadeca-12(19),13(18),14,16-tetraen-10-ylcarbamoyl)hexanamide (1.0 g, 1.83 mmol) was taken up in a solution of 20% THF in ethanol (500 mL) and then Pd on activated charcoal (200 mg) was added portionwise. The resulting slurry was stirred as $H_2$ gas was gently bubbled through the solution. After 4 hours, the reaction mixture was suction filtered through a bed of celite (1.5 cm), and the filtrate was concentrated and then taken up in methanol (30 mL) and filtered through a plug of cotton. Recrystallization from methanol/ethyl acetate/ether/petroleum ether gave (3R,10S)-N-hydroxy-5-methyl-3-(9-oxo-1,8-diaza-tricyclo[10.6.1.0$^{13,18}$]nonadeca-12(19),13(18),14,16-tetraen-10-yl-carbamoyl)hexanamide (768 mg, 92%), MS: 455 (M−H)$^+$.

D. In a similar manner, but replacing (3R,10S)-N-benzyloxy-5-methyl-3-(9-oxo-1,8-diazatricyclo[10.6.1.0$^{13,18}$]nonadeca-12(19),13(18),14,16-tetraen-10-ylcarbamoyl)hexanamide with the appropriate compound of formula (Ic), the following compounds of formula (Id) were prepared:

(3R,10S)-N-hydroxy-2-methoxycarbonyl-5-methyl-3-(9-oxo-1,8-diaza-tricyclo[10.6.1.0$^{13,18}$]nonadeca-12 (19),13(18),14,16-tetraen-10-ylcarbamoyl)hexanamide, MS: 515 (M+H)$^+$;

(3R,10S)-N-hydroxy-6-phenyl-3-(9-oxo-1,8-diazatricyclo[10.6.1.0$^{13,18}$]-nonadeca-12(19),13(18),14,16-tetraen-10-ylcarbamoyl)hexanamide, MS: 517 (M−H)$^−$;

(3R,10S)-N-hydroxy-2-aminocarbonyl-5-methyl-3-(9-oxo-1,8-diazatricyclo-[10.6.1.0$^{13,18}$]nonadeca-12(19),13(18),14,16-tetraen-10-ylcarbamoyl) hexanamide, MS: 483 (MH$^+$)—$H_2O$;

(3R,10S)-N-hydroxy-3-(9-oxo-1,8-diazatricyclo-[10.6.1.0$^{13,18}$]-nonadeca-12(19),13(18),14,16-tetraen-10-ylcarbamoyl) hexanamide, MS: 443 (MH$^+$);

(3R,9S)-5-methyl-3-(8-oxo-1,7-diaza-tricyclo[9.6.1.0$^{12,17}$] octadeca-11(18),12(17),13,15-tetraen-9-ylcarbamoyl) hexanamide; and (3RS,10S)-N-hydroxy-N-formyl-5-methyl-3-(9-oxo-1,8-diaza-tricyclo[10.6.1.0$^{13,18}$]nonadeca-12(19),13(18),14,16-tetraen-10-ylcarbamoyl)hexylamine, MS: 455 (M−H).

EXAMPLE 9

Compounds of Formula (Ie)

A. To a solution of 4-methyl-2-acetylthiomethylpentanoic acid (612 mg, 3 mmol), (10S)-10-amino-(9-oxo-1,8-diazatricyclo[10.6.1.0$^{13,18}$]nonadeca-12(19),13(18),14,16-tetraene (427 mg, 1.5 mmol), and HOBt·H$_2$O (230 mg, 1.5 mmol) in dry DMF (30 mL) under argon at room temperature was added EDCI (863 mg, 4.5 mmol) in one portion. After stirring overnight, DMF was removed at 30° C. under high vacuum to give a yellowish semi-solid. It was dissolved in ethyl acetate (50 mL), washed with 1N HCl (30 mL), 5% NaHCO$_3$ solution (30 mL) and finally brine (30 mL). The organic layer was dried (MgSO$_4$) and evaporated to dryness. The resulting pale yellow-oil was stirred in 50% ether-pet. ether (40 mL) to yield 600 mg (85%) of (10S)-2-acetylthiomethyl-4-methyl-N-(9-oxo-1,8-diaza-tricyclo[10.6.1.0$^{13,18}$]nonadeca-12(19),13(18),14,16-tetraen-10-yl) pentanamide as 1:1 stereoisomeric mixture. The stereoisomeric mixture was separated in flash column chromatography (LPS-2), eluted with 20% ethyl acetate in pet. ether to give the less polar stereoisomer, m.p. 226° C., and the more polar stereoisomer, m.p. 220° C.

EXAMPLE 10

Compounds of Formula (If)

A. To a solution of the less polar stereoisomer of (10S)-2-acetylthiomethyl-4-methyl-N-(9-oxo-1,8-diazatricyclo[10.6.1.0$^{13,18}$]nonadeca-12(19),13(18),14,16-tetraen-10-yl) pentanamide (50 mg, 0.106 mmol) in 10 mL of methanol at 0° C. under argon was added 0.5 mL concentrated NH$_4$OH. The reaction mixture was stirred from 0° C. (ice-bath was removed after addition of NH$_4$OH) to room temperature and further stored at room temperature for 1 hour. Excess methanol was removed under reduced pressure to give a white solid residue. The residue was partitioned between ethyl acetate (30 mL) and 0.1 NHCl (15 mL). The organic layer was washed with brine (15 mL), dried (MgSO$_4$), and evaporated to dryness. The solid residue was stirred in 50% ether/pet. ether and filtered to yield the more polar stereoisomer of (10S)-2-mercaptomethyl-4-methyl-N-(9-oxo-1,8-diazatricyclo[10.6.1.0$^{13,18}$]-nonadeca-12(19),13(18),14,16-tetraen-10-yl)pentanamide as a white powder, 41 mg (90%) m.p. 224° C.

EXAMPLE 11

Compounds of Formula (HH)

A. To 4-methylpentanoic acid (25 g, 0.215 mmol) in a 25° C. water bath, thionyl chloride (20.4 mL, 1.3 g) was slowly added. Then the mixture was heated at 50° C. under argon for 3 hours (until the evolution of gas had stopped). The crude reaction mixture was distilled at atmospheric pressure to give 4-methylpentanoyl chloride (25.3 g, 87.3%), b.p. 143° C.

B. In a similar manner, but replacing 4-methylpentanoic acid with 5-phenylpentanoic acid (5 g), 5-phenylpentanoyl chloride was prepared (4.4 g), as a colorless liquid, b.p. 910–930° C.

EXAMPLE 12

Compounds of Formula (N)

A. To a suspension of 60% NaH (836 mg, 1.5 eq.) in toluene (200 mL) at room temperature under argon was added L-(+)-2,10-camphorsultam (3.0 g, 3.9 mmol) portionwise. The mixture was stirred vigorously at room temperature for one hour. Then 4-methylpentanoyl chloride was carefully added dropwise to the solution at 0° C. After stirring the reaction at room temperature for 3 hours, the reaction was quenched with 10 mL of water, and 70 mL of ether was added. The reaction mixture was first washed with 0.5N HCl (2×50 mL), then 5% K$_2$CO$_3$ (3×50 mL) and finally with brine (1×50 mL). The organic layer was dried over MgSO$_4$, filtered and evaporated to dryness. Purification by column chromatography (1:6 ethyl acetate/petroleum ether as eluant) gave N-4-methylpentanoyl-L-(+)-2,10-camphor sultam (3.39 g, 78%).

B. In a similar manner, but replacing 4-methylpentanoyl chloride with the appropriate chloride, the following compounds of formula (N) were prepared:
N-3-phenylpropanoyl-L-(+)-2,10-camphor sultam, MS: 347 (M$^+$);
N-5-phenylpentanoyl-L-(+)-2,10-camphor sultam, MS: 375 M$^+$;
N-pentanoyl-L-(+)-2,10-camphor sultam, MS: 300 (M+H)$^+$.

EXAMPLE 13

Compounds of Formula (Q)

A. To a solution of N-4-methylpentanoyl-L-(+)-2,10-camphor sultam (3.39 g, 10.8 mmol) in 75 mL of dry THF at −78° C. under argon was added NaN(TMS)$_2$ (1.0 M in THF, 11.34 mL, 1.05 eq.) dropwise over five minutes. After stirring at −78° C. for 1 hour, hexamethylphosphoramide (5 mL) was added to the mixture, followed by t-butylbromoacetate (5.2 ml, 3 eq), then 400 mg of tetra n-butyl ammonium iodide was added in one portion. The resulting solution was kept at −78° C. under argon overnight. The next morning, the reaction was quenched with water (100 mL), and then it was extracted with ether (3×100 mL). The combined ether layers were washed with brine, then dried over Na$_2$SO$_4$, filtered and concentrated. Purification by column chromatography (5:95 ethyl acetate/petroleum ether to 10:90 ethyl acetate/petroleum ether as eluant) gave N-(4-methyl-2-t-butoxycarbonylmethyl)pentanoyl-L-(+)-2,10-camphor sultam (4 g, 86.5%).

B. In a similar manner, but replacing N-4-methylpentanoyl-L-(+)-2,10-camphor sultam with the appropriate compound of formula (N), the following compounds of formula (Q) were prepared:
N-(3-phenyl-2-t-butoxycarbonylmethyl)propanoyl-L-(+)-2,10-camphor sultam, MS: 461 (M$^+$);
N-(5-phenyl-2-t-butoxycarbonylmethyl)pentanoyl-L-(+)-2,10-camphor sultam, MS: 490 (M+H)$^+$;
N-(2-t-butoxycarbonylmethyl)pentanoyl-L-(+)-2,10-camphor sultam, MS: 414 (M+H)$^+$.

EXAMPLE 14

Compounds of Formula (Ka)

A. To a stirred solution of N-(4-methyl-2-t-butoxycarbonylmethyl)pentanoyl-L-(+)-2,10-camphor sultam (5.45 g, 12.7 mmol) in 50% aqueous THF (150 mL) at 0° C. under argon was added LiOH H$_2$O crystals (2.14 g, 4 eq.) followed by 30% H$_2$O$_2$ (11.5 mL). Then the ice-bath was removed and the resulting emulsion was stirred for 3 hours before it had turned clear. Most of the THF was removed under reduced pressure at 35° C. Then CH$_2$Cl$_2$ (150 mL) was added and with stirring 4N HCl was added to pH=2. After adding NaCl, the aqueous layer was further extracted with CH$_2$Cl$_2$ (3×150 mL). The CH$_2$Cl$_2$ was removed under reduced pressure at 35° C. and then the residue was taken up in ethyl acetate (150 mL). This solution was then extracted with 5% K$_2$CO$_3$ (3×50 mL) and the combined extracts were washed with ether (50 mL). Then CH$_2$Cl$_2$ was added to the aqueous layer and with stirring with Nacl, the aqueous layer was extracted with CH$_2$Cl$_2$ (3×70 mL) and the combined extracts were dried over Na$_2$SO$_4$, filtered and concentrated to give (2R)-4-methyl-2-t-butoxycarbonylmethyl-pentanoic acid as a colorless oil (2.95 g, quantitative yield).

B. In a similar manner, but replacing N-(4-methyl-2-t-butoxycarbonylmethyl)pentanoyl-L-(+)-2,10-camphor sultam with the appropriate compound of formula (Q), the following compounds of formula (Ka) were prepared:

(2R)-3-phenyl-2-t-butoxycarbonylmethyl-propanoic acid, MS: 265 (M+H)$^+$;

(2R)-5-phenyl-2-t-butoxycarbonylmethyl-pentanoic acid, MS: 293 (M+H)$^+$;

(2R)-2-t-butoxycarbonylmethyl-pentanoic acid, (colorless oil, 1.09 g).

C. (2R)-3-Phenyl-2-t-butoxycarbonylmethyl-propanoic acid (55 mg) was taken up in glacial acetic acid (20 mL) and PtO$_2$ (25 mg) was added in acetic acid. Then the beaker was placed in a Parr bomb, it was evacuated and charged with 100 psi of H$_2$. After stirring for 3 days, the mixture was suction filtered through a 1 cm bed of celite. The filtrate was then concentrated to a yellow oil, (2R)-3-cyclohexyl-2-t-butoxycarbonylmethyl-propanoic acid (56 mg), MS: 269 (M-H)$^-$.

EXAMPLE 15

Compound of Formula (R)

To a solution of D-leucine (50 g, 0.381 mol) in 570 mL of 3N HBr (aq) at 0° C. was added sodium nitrite (42 g, 1.6 eq) portion-wise over 1 hour and 15 minutes. The reaction was further stirred for 3 hrs at 0° C. then it was extracted with ether (1000 mL). After washing the ether layer with water (2×500 mL) it was dried over MgSO$_4$ and concentrated. The red syrup was then co-evaporated with chloroform (3×200 mL) to remove the color and then it was pumped to give (2R)-2-bromo-4-methylpentanoic acid, as a colorless oil with a constant weight of 71.3 g.

EXAMPLE 16

Compound of Formula (S)

Into dichloromethane (80 mL) was condensed isobutene to double the volume (at −50° C. CHCl$_3$/dry ice). To this solution was added (2R)-2-bromo-4-methylpentanoic acid (28 g, 143.6 mmol) and maintaining the temperature between −400 and −50° C. concentrated sulphuric acid (1 mL) was added dropwise. The reaction was then allowed to warm to room temperature over 20 hours. The solution was then concentrated before adding additional methylene chloride (300 mL) which was subsequently washed with saturated NaHCO$_3$ (2×100 mL) followed by water (2×100 mL). After drying over Na$_2$SO$_4$, the organic layer was filtered and concentrated to give a yellow oil. The material was distilled to give 23 g of (2R)-2-bromo-4-methylpentanoic acid t-butyl ester as a clear colorless oil.

EXAMPLE 17

Compound of Formula (U)

To benzyl methyl malonate (2.13 mL, 1 eq) and potassium-t-butoxide (1.36 g, 1 eq) in dry DMF (100 mL) at 0° C. was added (2R)-2-bromo-4-methylpentanoic acid t-butyl ester (2.89 g, 11.5 mmol) in 50 mL of DMF dropwise over a period of 1 hr. The resulting solution was then stirred at 0° C. for 3 days. Then the reaction mixture was partitioned between ether (150 mL) and saturated ammonium chloride (80 mL). The resulting mixture was suction filtered through celite and the two phases were separated. Then the aqueous layer was further extracted with ether (3×100 mL) and the combined ether extracts were washed with water (6×100 mL). After drying over MgSO$_4$, the organic layer was filtered and evaporated to dryness. Purification by flash column-chromatography (eluting with 4:96 ethyl acetate/petroleum ether) gave (2R)-2-[(1-methoxy-carbonyl-1-benzyloxycarbonyl)methyl]-4-methylpentanoic acid t-butyl ester (2.55 g) as a clear colorless oil, MS: 322 (M-acetone)$^+$.

EXAMPLE 18

Compound of Formula (Kb)

(2R)-2-[(1-Methoxycarbonyl-1-benzyloxycarbonyl)-methyl]-4-methylpentanoic acid t-butyl ester was taken up in 5 mL of 80% TFA (eq) at room temperature and stirred for 1.5 hrs by TLC. The reaction was only 30% complete so additional TFA (10 mL) was added. Within ½ hour, the reaction was complete. The TFA was removed under high vacuum at 45° C. and the residue was taken up in ethyl acetate and washed with water (5×30 mL). After drying over Na$_2$SO$_4$, the ethyl acetate layer was filtered, concentrated and pumped to yield (2R)-2-[(1-methoxycarbonyl-1-benzyloxycarbonyl)methyl]-4-methylpentanoic acid, as a solid (1.68 g), MS: 322 (M$^+$).

EXAMPLE 19

Compound of Formula (W)

Crystalline phosphinic acid (8.4 g, 0.13 mol) was stirred in neat triethylorthoformate (22 mL, 0.20 ml) for 90 minutes at room temperature. This was then transferred via cannula to a stirred solution of ethylisobutylacrylate (8 g, 0.036 mol) and tetramethylguanidine (4.5 mL, 0.036 mol) that had been cooled to 0° C. for 10 minutes. The ice bath was removed and the reaction stirred for 4 hours. The mixture was diluted with 200 ml of diethyl ether and the solution washed with 1 N HCl (100 ml), water (4×100 ml) brine (100 ml), and dried over magnesium sulfate. Evaporation under reduced pressure yielded 8.15 g of 2-(ethoxy)-phosphinoylmethyl-4-methylpentanoic acid ethyl ester as a slightly yellow colored oil, MS: 349 (M–H$_2$O)$^+$.

EXAMPLE 20

Compound of Formula (X)

Crude 2-(ethoxy)phosphinoylmethyl-4-methylpentanoic acid ethyl ester (26 g) was dissolved in 600 mL THF/CH$_2$Cl$_2$ (50/50) and cooled to 0° C. Diisopropyl-ethylamine (32 mL) and 90.8 mL of bis-(trimethylsilyl) acetamide were then added to the solution and the resulting mixture was stirred for 20 minutes before paraformaldehyde (5.5 g) was added. The solution was brought to room temperature and heated at 37° C. for 18 hours. The solvent was removed by evaporation, and the resulting oil dissolved in 200 mL ethyl acetate. The solution was washed with 50 mL of 1N HCl (2×), 50 mL of brine (2×), dried over MgSO$_4$, filtered and evaporated to yield 19.3 g of 2-(ethoxy)(hydroxymethyl) phosphinoylmethyl-4-methylpentanoic acid ethyl ester as a faintly yellow oil, MS: 281 (MH$^+$).

Example 21

Compounds of Formula (Y)

A. 2-(Ethoxy)(hydroxymethyl)phosphinoylmethyl-4-methylpentanoic acid ethyl ester (5 g) was dissolved in 20 mL of $CH_2Cl_2$ and cooled to $-20°$ C. (in duplicate). Methanesulfonyl chloride (1.5 mL) and triethylamine (3.0 mL) were added to solution dropwise. After 15 minutes the bath was removed and the reaction left at room temperature for 3½ hours. Each solution was then washed with 10 mL cold 2% HCl, 10 mL $NaHCO_3$ (sat), 10 mL brine, dried with $MgSO_4$, filtered and evaporated to yield 12.8 g (combined yield) of 2-(ethoxy)(methane-sulfonyloxymethyl)phosphinoylmethyl-4-methylpentanoic acid ethyl ester.

B. In a similar manner, but replacing methanesulfonyl chloride with p-toluenesulfonyl chloride, 2-(ethoxy)(p-toluenesulfonyloxymethyl)phosphinoylmethyl-4-methylpentanoic acid ethyl ester is prepared.

EXAMPLE 22

Compounds of Formula (AA)

Sodium hydride (1.52 g, (60%)) and 6 g of 2-quinoline thiol were stirred together at 0° C. in 50 mL DMF. After the initial $H_2$ evolution had subsided, the mixture was stirred at room temperature for 2½ hours. The mixture was then cooled to 0° C. and 2-(ethoxy)(methanesulfonyloxy-methyl)phosphinoyl-methyl-4-methylpentanoic acid ethyl ester (12.8 g) in 10 mL DMF was added via cannula and the resulting mixture was then stirred for 18 hours, slowly warming to room temperature. The DMF was removed by evaporation, the residue dissolved in 50 mL ethyl acetate and washed with 50 mL $H_2$ (2x), brine (50 mL), dried with $MgSO_4$ and evaporated to a yellow semi-solid. Purification by flash chromatography using 10% ethyl acetate/hexane to 80% ethyl acetate/hexane for the elution yielded 10 g of 2-(ethoxy)(quinolin-2-ylthiomethyl)-phosphinoyl-methyl-4-methylpentanoic acid ethyl ester (Rf 0.35 80% ethyl acetate/hexane), MS: 424 (MH$^+$).

B. In a similar manner, but replacing 2-quinolinethiol with 1-naphthalenethiol, 2-naphthalenethiol or thiophenol, the following compounds of formula (AA) are prepared:
2-(ethoxy)(naphth-1-ylthiomethyl)phosphinoyl-methyl-4-methylpentanoic acid ethyl ester;
2-(ethoxy)(naphth-2-ylthiomethyl)phosphinoyl-methyl-4-methylpentanoic acid ethyl ester; and
2-(ethoxy)(phenylthiomethyl)phosphinoyl-methyl-4-methylpentanoic acid ethyl ester.

EXAMPLE 23

Compounds of Formula (BB)

A. 2-(Ethoxy)(quinolin-2-ylthiomethyl)-phosphinoyl-methyl-4-methylpentanoic acid ethyl ester (4.5 g) was dissolved in 100 mL THF and 12.5 mL of 2N NaOH was added together with enough methanol to make the solution homogeneous. After 18 hours the THF was removed by evaporation, the residue diluted with 50 mL $H_2O$ and washed with 50 mL ethyl acetate. The aqueous phase was then acidified to pH 4, and the product extracted with 50 mL ethyl acetate (2x). The ethyl acetate was washed with 20 mL brine, dried with $MgSO_4$ and evaporated to yield 3.8 g of 2-(hydroxy)(quinolin-2-ylthiomethyl)-phosphinoyl-methyl-4-methylpentanoic acid as a yellow oil, MS: 368 (MH$^+$).

B. In a similar manner the following compounds of formula (BB) are prepared:
2-(hydroxy)(naphth-1-ylthiomethyl)phosphinoyl-methyl-4-methylpentanoic acid;
2-(hydroxy)(naphth-2-ylthiomethyl)phosphinoyl-methyl-4-methylpentanoic acid; and
2-(hydroxy)(phenylthiomethyl)phosphinoyl-methyl-4-methylpentanoic acid.

EXAMPLE 24

Resolution of a Compound of Formula (BB)

2-(Hydroxy)(quinolin-2-ylthiomethyl)phosphinoyl-methyl-4-methylpentanoic acid (5.3 g) was dissolved in 50 mL of warm ethanol (abs) and 4.2 g of (−)-cinchonidine was added. After 30 minutes at room temperature the salt began to precipitate out. The flask was covered in foil and allowed to stand for 2 days. The salt was then removed by suction filtration, and the filtrate evaporated to a yellow foam. The salt and the filtrate were each dissolved in 100 mL ethyl acetate and washed successively with 1% HCl to remove the cinchonidine while keeping the pH above 4. Both solutions were each dried over $MgSO_4$ and evaporated to yield 2.4 g of a single stereoisomer, $[\alpha]_D^{24}$=+10.68° (9.73 mg in methanol (2 mL)) and 2.5 g of the other single stereoisomer, $[\alpha_D^{24}$=−8.70° (9.88 mg in methanol (2 mL)).

EXAMPLE 25

Compound of Formula (Ig)

A single stereoisomer of 2-(hydroxy)(quinolin-2-ylthiomethyl)-phosphinoylmethyl-4-methylpentanoic acid (300 mg, 0.81 mmol) and 1,1'-carbonyldiimidazole (174 mg, 1.0 mmol) were stirred at 0° C. in 6 mL THF for 1½ hours. (10S)-10-Amino-(9-oxo-1,8-diazatricyclo[10.6.1.0$^{13,18}$] nonadeca-12(19),13(18),14,16-tetraene (270 mg, 0.95 mmol) was added to the solution and the resulting mixture was allowed to warm to room temperature and then stirred for 18 hours. The THF was removed by evaporation and the residue dissolved in 60 mL ethyl acetate. The ethyl acetate was washed with 10 mL $H_2O$, 10 mL brine, dried with $MgSO_4$ and evaporated to yield (10S)-(4-methyl-2-(9-oxo-1,8-diazatricyclo[10.6.1.0$^{13,18}$]nonadeca-12(19),13(18), 14,16-tetraen-10-ylcarbamoyl)pentyl](quinolin-2-ylthiomethyl)phosphinic acid as a yellow oil. Purification was carried out by reverse phase HPLC using a gradient of acetonitrile and 50 mm $NH_4OAc$ buffer as the eluents. The more polar stereoisomer was isolated (30 mg) at 41% acetonitrile, and the less polar stereoisomer (10 mg) at 43% acetonitrile. The fractions were lyophilized to off-white powders, MS: 635 (MH$^+$).

EXAMPLE 26

Compound of Formula (Ih)

(3R,10S)-5-Methyl-3-(9-oxo-1,8-diazatricyclo [10.6.1.0$^{13,18}$]nonadeca-12(19),13(18),14,16-tetraen-10-ylcarbamoyl)hexanoic acid (200 mg, 0.45 mmol) was dissolved in 10 mL of glacial acetic acid and was hydrogenated at 100 psi $H_2$ pressure in the presence of $Pt_2O$ (60 mg) in a Parr reactor at room temperature for 15 hrs. Argon gas was bubbled into the reaction mixture for 15 mins. and the catalyst ($Pt_2O$) was filtered off (through a cone of celite). The clear filtrate was evaporated to dryness and further co-evaporated with toluene twice to give quantitative yield of (3R,10S)-5-methyl-3-(9-oxo-1,8-diazatricyclo [10.6.1.0$^{13,18}$]nonadecan-10-ylcarbamoyl)hexanoic acid as a white solid. MS: 448 (M−H)$^-$.

EXAMPLE 27

Compound of Formula (Ii)

To (3R,10S)-5-methyl-3-(9-oxo-1,8-diazatricyclo-[10.6.1.0$^{13,18}$]-nonadecanylcarbamoyl)hexanoic acid and O-benzylhydroxylamine (5 eq, 2.25 mmol, 277 mg) in 10 mL of dry DMF at room temperature were added 1-hydroxybenzo-triazoleH$_2$O (2 eq, 0.9 mmol, 122 mg) and EDCI (5 eq, 2.25 mmol, 431 mg). The resulting clear reaction mixture was stirred at room temperature overnight. The solvent was removed under high vacuum at room temperature and the residue was partitioned between ethyl acetate (15 mL) and 1N HCl (15 mL). The ethyl acetate layer was further extracted with 1N HCl (15 mL). The combined aqueous extract was basified with 4N NaOH to pH 10 and was saturated with NaCl and extracted with CH$_2$Cl$_2$ (3×15 ml). The combined CH$_2$Cl$_2$ extract was dried (MgSO$_4$), filtered, and evaporated to dryness to give a semi-solid. The semi-solid was stirred in ether (10 mL) at 0° C. for 30 minutes and filtered to yield 85 mg (34%) of (3R,10S)-N-hydroxy-5-methyl-3-(9-oxo-1,8-diazatricyclo[10.6.1.0$^{13,18}$]-nonadecanylcarbamoyl)hexanamide, as a white powder, MS: 555 (M+H)$^+$.

EXAMPLE 28

Compound of Formula (Ij)

(3R,10S)-N-benzyloxy-5-methyl-3-(9-oxo-1,8-diazatricyclo-[10.6.1.0$^{13,18}$]nonadecan-10-ylcarbamoyl) hexanamide (75 mg, 0.135 mmol) was hydrogenated at 1 atm H$_2$ pressure in absolute ethanol (5 mL) in the presence of 10% Pd-C (35 mg) for 2 hours. Argon gas was bubbled into the reaction mixture for 10 minutes and the reaction mixture was filtered through a cone of celite. The catalyst on celite was further washed with 5 mL of ethanol. The combined filtrate was evaporated to dryness to afford a solid residue. The solid was stirred in 10 mL of 5% MeOH in ether at 0° C. for 30 mins and filtered to yield 57 mg (91%) of (3R,10S)-N-hydroxy-5-methyl-3-(9-oxo-1,8-diaza-tricyclo [10.6.1.0$^{13,18}$]nonadecan-10-ylcarbamoyl) hexanamide, as an off-white powder, MS: 465 (M+H)$^+$.

EXAMPLE 29

Compound of Formula (DD)

To N-t-butoxycarbonyltryptophan (3 mmol, 914 mg) and N-methylethanediamine (3.6 mmol, 0.27 g, 0.32 mL) in dry DMF (15 mL) were added 1-hydroxybenzotriazoleH$_2$O (3 mmol, 459 mg) and EDCI (4.5 mmol, 863 mg). The mixture was stirred at room temperature overnight under argon and excess of the solvent (DMF) was removed under high vacuum at 35° C. The residue was dissolved in ethyl acetate (40 mL) and the adduct was extracted into 1N HCl (3×25 mL). The combined aqueous extract was basified with solid K$_2$CO$_3$ and extracted with ethyl acetate (3×25 mL). The combined organic extract was washed with brine (30 mL) and dried (MgSO$_4$). Evaporation to dryness yielded 920 mg (85%) HPLC pure product, N'-t-butoxycarbonyltrytophan-N-((methyl)aminoethyl)-amide as a white foam.

EXAMPLE 30

Compound of Formula (EE)

To a vigorously stirred solution of N'-t-butoxycarbonyl-trytophan-N-((methyl)aminoethyl)-amide (2 g, 5.55 mmol) and trans-1,4-dichlorobut-2-ene (8.32 mmol, 1.04 g, 0.88 mL) in methylene chloride (75 mL) and 40% KOH (50 mL) was added 0.3 equivalents of benzyltriethyl ammonium chloride (1.66 mmol, 378 mg). After stirring at room temperature overnight, the yellowish organic layer was separated and the aqueous layer further extracted with 30 mL of CH$_2$Cl$_2$. The combined methylene chloride extract was washed with brine and dried (MgSO$_4$). The residue was dissolved in 10 mL of MeOH and at 0° C. will stirring 50 mL of ether was added. The resulting yellow solid was filtered off. The filtrate was evaporated to dryness to give 1.12 g HPLC pure product, 11-N'-(t-butoxycarbonyl)amino-10-oxo-1,6,9-triaza-6-methyl-tricyclo[11.6.1.0$^{14,19}$]eicosa-3 (4),13(20),14(19),15,17-pentaene as a pale yellow powder, MS: 413 (M+H)$^+$.

EXAMPLE 31

Compound of Formula (FF)

11-N'-(t-Butoxycarbonyl)amino-10-oxo-1,6,9-triaza-6-methyl-tricyclo[11.6.1.0$^{14,19}$]eicosa-3(4),13(20),14(19),15, 17-pentaene (414 mg mmol) was stirred in 40% TFA in CH$_2$Cl$_2$ (10 mL) at room temperature for 1 hr. Excess of TFA and solvent were removed under reduced pressure. The residue was dissolved in methylene chloride (30 mL) and washed with 5% K$_2$CO$_3$ solution (2×15 ml) and brine (15 mL). The organic layer was dried (MgSO$_4$) and evaporated to give 240 mg (76%) of pale yellow foam, 11-amino-10-oxo-1,6,9-triaza-6-methyltricyclo[11.6.1.0$^{14,19}$]eicosa-3(4), 13(20),14(19),15,17-pentaene, MS: 313 (M+H)$^+$.

EXAMPLE 32

Compounds of Formula (Ik)

11-Amino-10-oxo-1,6,9-triaza-6-methyltricyclo [11.6.1.0$^{14,19}$]eicosa-3(4),13(20),14(19),15,17-pentaene (161 mg, 0.7 mmol) and (2R)-4-methyl-2-t-butoxycarbonylmethylpentanoic acid (220 mg, 0.7 mmol) was stirred in dry DMF (15 mL) in the presence of HOBt (0.7 mmol). EDCI (1.4 mmol, 268 mg), and N-methyl morpholine (1.4 mmol, 0.15 mL) under argon at room temperature overnight. Excess of DMF was removed under reduced pressure. The residue was dissolved in methylene chloride (30 mL) and washed with water (30 mL). The aqueous wash was extracted with CH$_2$Cl1 (30 mL). The combined methylene extract was dried (Mg SO$_4$) and evaporated to give a light brown oil. The light brown oil was purified reverse-phase HPLC (C$_{18}$ column; CH$_3$CN—50 MM NH$_4$OH$_2$ gradient). The desired fraction was lyophilized to give 148 mg (40%) of (3R,11S)-5-methyl-3-(10-oxo-1,6,9-triaza-6-methyltricyclo-[11.6.1.0$^{14,19}$]eicosa-3 (4),13(20),14(19),15,17-pentaen-11-ylcarbamoyl)hexanoic acid t-butyl ester as a pale yellow powder, MS: 525.2 (M+H)$^+$.

EXAMPLE 33

Compound of Formula (II)

(3R,11S)-5-Methyl-3-(10-oxo-1,6,9-triaza-6-methyltricyclo-[11.6.1.0$^{14,19}$]eicosa-3(4),13(20),14(19),15, 17-pentaen-11-ylcarbamoyl)-hexanoic acid t-butyl ester (0.228 mmol, 120 mg) was stirred in 20% TFA in CH$_2$Cl$_2$ (5 mL) at room temperature for 1 hr. Excess solvent was removed under reduced pressure (rotary evaporator at 30° C.) to give the crude acid, (3R,11S)-5-methyl-3-(10-oxo-1, 6,9-triaza-6-methyltricyclo-[11.6.1.0$^{14,19}$]eicosa-3(4),13 (20),14(19),15,17-pentaen-11-ylcarbamoyl)hexanoic acid, as a light brown oil. Purification by reverse-phase HPLC, eluted with $CH_3CN$—$NH_4OAc$ buffer under gradient conditions yielded 90 mg (75%) of the acid as pale yellow powder, MS: 469.1 $(M+H)^+$.

EXAMPLE 34

Compound of Formula (Im)

(3R,11S)-5-Methyl-3-(10-oxo-1,6,9-triaza-6-methyltricyclo-[11.6.1.0$^{14,19}$]eicosa-3(4),13(20),14(19),15,17-pentaen-11-ylcarbamoyl)hexanoic acid and O-benzylhydroxylamine (5 eq, 2.5 mmol, 308 mg) were stirred in dry DMF (30 mL) in the presence of HOBt (2 eq, 1 mmol, 135 mg), EDCI (5 eq, 2.5 mmol, 479 mg), and N-methylmorpholine (10 eq, 5 mmol, 0.55 mL) at room temperature under argon for 15 hours. The solvent was removed under high vacuum at room temperature. The residue was dissolved in distilled water (35 mL) and was extracted with 10% ethyl acetate in pet. ether to remove less polar impurities. The expected product was then extracted from the aqueous layer with $CH_2Cl_2$ (2×35 mL). The organic extract was washed with brine (25 mL), dried ($MgSO_4$) and evaporated to give a yellow oil (330 mg). The crude product was purified on reverse-phase HPLC ($CH_3CN$—$NH_4OAc$ buffer; gradient) and lyophilized to yield 175 mg (61%) of (3R,11S)-N-benzyloxy-5-methyl-3-(10-oxo-1,6,9-triaza-6-methyl-tricyclo-[11.6.1.0$^{14,19}$]eicosa-3(4),13(20),14(19),15,17-pentaen-11-ylcarbamoyl)hexanamide as an off-white powder, MS: 572 $(M-H)^-$.

EXAMPLE 35

Compound of Formula (In)

A mixture of (3R,11S)-N-benzyloxy-5-methyl-3-(10-oxo-1,6,9-triaza-6-methyltricyclo-[11.6.1.0$^{14,19}$]eicosa-3(4),13(20),14(19),15,17-pentaen-11-ylcarbamoyl)hexanamide (40 mg, 0.07 mmol) and 10% Pd-C (10 mg) was stirred in a solution of 3% HCOOH in ethanol (5 mL) at room temperature for 1 hour. The mixture was filtered through a cone of celite and concentrated in vacuo. To the solid residue in 1 mL of 50% AcOH/MeOH with stirring was added 5 mL of ether in one portion. The off-white powder was then collected by filtration to give 26 mg (68%) of (3R,11S)-N-hydroxy-5-methyl-3-(10-oxo-1,6,9-triaza-6-methyltricyclol [11.6.1.0$^{14,19}$]eicosa-3(4),13(20),14(19),15,17-pentaen-11-ylcarbamoyl)hexanamide, MS: 488.5 $(MH^+)$.

EXAMPLE 36

Compounds of Formula (JJ)

A. To a solution of (±)-2-hydroxybutanoic acid, sodium salt (2.54 g, 20.1 mmol) in dry DMF (30 ml) was added benzyl bromide (2.9 mL, 1.2 eq) and anhydrous KI (330 mg, 0.1 eq). The suspension was heated at 100° C. for 24 hours and the DMF was distilled off under reduced pressure. The residue was taken up in ether, washed with water and saturated $Na_2S_2O_3$, dried ($MgSO_4$), and concentrated. Distillation of the residual oil afforded 3.7 g (95%) of benzyl (±)-2-hydroxybutanoate as a colorless oil, b.p. 95° C. (0.45 Torr).

B. Alternatively, to a cold (0° C.) suspension of NaH (3.8 g of a 60% weight dispersion in mineral oil, 95.0 mmol) in THF (50 mL) was added a solution of glycolic acid (7.2 g, 95 mmol) in THF (50 mL) dropwise via cannula. The resulting solution was warmed to 25° C. and concentrated in vacuo. The resulting salt was suspended in DMF (100 mL) and treated with KI (1.57 g, 0.1 eq) and benzyl bromide (12.3 mL, 1.1 eq). The mixture was heated at 100° C. for 23 hours under argon and the DMF was evaporated. The residue was dissolved in ether and washed with water, saturated $Na_2S_2O_3$, and brine, and dried over $MgSO_4$. Distillation afforded benzyl glycolate (8.5 g, 54%) as a colorless oil, b.p. 85–87° C. (0.5 Torr).

EXAMPLE 37

Compounds of Formula (LL)

A. To a cold (0° C.) solution of benzyl (±)-2-hydroxybutanoate (1.75 g, 9.01 mmol) in $CH_2Cl_2$ (50 mL) was added 2,6-lutidine (1.2 mL, 1.1 eq) followed by triflic anhydride (1.7 mL, 1.1 eq) dropwise. After 10 minutes, a solution of L-leucine t-butyl ester (1.7 g, 1 eq) and diisopropylethyl-amine (1.7 mL, 1.1 eq) in $CH_2Cl_2$ (30 mL) was added dropwise at 0° C. The solution was warmed to 25° C. for 36 hours, diluted with $CH_2Cl_2$, and washed with saturated $NaHCO_3$ (50 mL). After drying ($Na_2SO_4$) and concentration in vacuo, the residual oil was flash chromatographed (silica, 5% ethyl acetate/hexanes) to separate diastereomers. The less polar diastereomer, (1R)-N-(2-benzyloxycarbonyl)propyl-L-leucine t-butyl ester ($R_f$ 0.22, 5% ethyl acetate/hexanes), and the more polar diastereomer, (1S)-N-(2-benzyloxycarbonyl)propyl-L-leucine t-butyl ester ($R_f$ 0.13), were further purified individually by HPLC (5% ethyl acetate/hexanes) to afford 1.1 g of the more polar diastereomer and 0.78 g of the less polar diastereomer, MS(FAB): 364 $(MH^+)$.

B. In a similar manner, from benzyl glycolate (379 mg, 2.7 mmol), L-leucine t-butyl ester (435 mg, 2.7 mmol), 2,6-lutidine (0.35 mL, 2.8 mmol), diisopropylethylamine (0.53 mL, 0.28 mmol), and triflic anhydride (0.51 mL, 2.8 mmol) there was obtained 383 mg (50%) of N-benzyloxycarbonyl-methyl-L-leucine t-butyl ester as a colorless oil, MS(FAB): 336 $(MH^+)$.

EXAMPLE 38

Compounds of Formula (Io)

A. To a solution of (1S)-N-(2-benzyloxycarbonyl)propyl-L-leucine t-butyl ester (143 mg, 0.393 mmol) in $CH_2Cl_2$ (3 mL) at 0° C. was added TFA (0.5 mL). The solution was stirred at 25° C. for 4 hours and then concentrated in vacuo to yield the salt of (1S)-N-(2-benzyloxycarbonyl)-propyl-L-leucine (compound of formula (MM)), which was then dissolved in DMF (3 mL) with (10S)-10-amino-(9-oxo-1,8-diazatricyclo[10.6.1.0$^{13,18}$]-nonadeca-12(19),13(18),14,16-tetraene (124 mg, 1.1 eq) and HOBT (80 mg, 1.5 eq). After cooling to 0° C., N-methylmorpholine (60 mL, 1.5 eq) and EDCI (113 mg, 1.5 eq) were added. After 18 hours at 25° C., the reaction mixture was diluted with 10 mL of ethyl acetate, washed with saturated $NaHCO_3$ (3×10 mL) and water (2×10 mL), dried ($Na_2SO_4$), and concentrated. The residue was flash chromatographed (silica, 1% MeOH/$CH_2Cl_2$) and fractions with $R_f$ 0.5 (5% MeOH/$CH_2Cl_2$) were collected. Reverse phase HPLC afforded (2R,1'S,10S)-2-[N-[(1-benzyloxycarbonyl)-propylamino]-4-methyl-N-(9-oxo-1,8-diaza-tricyclo-[10.6.1.0$^{13,18}$]nonadeca-12(19),13(18),14,16-tetraen-10-yl) pentanamide (46 mg), MS(FAB): 575 $(MH^+)$ B. In a similar manner, but substituting (1R)-N-(2-benzyloxycarbonyl)propyl-L-leucine t-butyl ester (270 mg) for (1S)-N-( 2-benzyloxycarbonyl)propyl-L-leucine t-butyl ester, there was obtained (2R,1'R,10S)-2-[N-(1- benzyloxycarbonyl)propylamino]-4-methyl-N-(9-oxo-1,8-diazatricyclo[10.6.1.0$^{13,18}$]nonadeca-12(19),13(18),14,16-tetraen-10-yl)pentanamide, (175 mg), MS(FAB): 575 (MH$^+$).

EXAMPLE 39

Compounds of Formula (Ip)

A. To a solution of (2R,1'S,10S)-2-[N-(1-benzyloxycarbonyl)-propylamino]-4-methyl-N-(9-oxo-1,8-diazatricyclo-[10.6.1.0$^{13,18}$]nonadeca-12(19),13(18),14,16-tetraen-10-yl)pentanamide (46 mg) in THF/MeOH (1:1, 2 mL) under argon was added 1 M barium hydroxide (0.3 mL). After 24 hours at 25° C., CO$_2$ was passed over the solution and the resulting precipitate of barium carbonate was filtered off. The solvents were removed under reduced pressure and the aqueous residue was adjusted to pH 5.5 with 1 M HCl. After removing the water, reverse phase HPLC afforded (2R,1'S,10S)-2-[N'-(1-Carboxy) propylamino]-4-methyl-N-(9-oxo-1,8-diazatricyclo [10.6.1.0$^{13,18}$]-nonadeca-12(19),13(18),14,16-tetraen-10-yl)pentanamide, as a white solid, MS(FAB): 483 (M–H)$^-$. In a similar manner were prepared:
(2RS,10S)-2-[Carboxymethylamino]-2-cyclohexyl-N-(9-oxo-1,8-diazatricyclo [10.6.1.0$^{13,18}$]nonadeca-12(19),13(18),14,16-tetraen-10-yl)acetanamide, 497 (M+H)$^+$.
(2RS,10S)-2-[Carboxymethylamino]-3-methyl-N-(9-oxo-1,8-diazatricyclo-[10.6.1.0$^{13,18}$]nonadeca-12(19),13(18),14,16-tetraen-10-yl)pentamide, 471 (M+H)$^+$.
(2RS,10S)-2-[Phosphonylmethylamino]-4-methyl-N-(9-oxo-1,8-diazatricyclo-[10.6.1.0$^{13,18}$]nonadeca-12(19),13(18),14,16-tetraen-10-yl)pentamide B. In a similar manner, from (2R,1'R,10S)-2-[N'-(1-benzyloxy-carbonyl)propylamino]-4-methyl-N-(9-oxo-1,8-diazatricyclo[10.6.1.0$^{13,18}$]-nonadeca-12(19),13(18),14,16-tetraen-10-yl)pentanamide, (2R,1'S,10S)-2-[N'-(1-carboxy)propylamino]-4-methyl-N-(9-oxo-1,8-diazatricyclo-[10.6.1.0$^{13,18}$]-nonadeca-12(19),13(18),14,16-tetraen-10-yl)pentanamide (16 mg) was obtained, MS(FAB): 483(M–H)$^-$.

C. Proceeding as in the preparation of compound of formula (Io) above, from N-[(benzyloxycarbonyl)methyl]-L-leucine t-butyl eater (156 mg, 0.465 mmol), HOBT (94 mg, 1.5 eq), EDCI (134 mg, 1.5 eq), N-methyl-morpholine (77 pL), and (10S)-10-amino-(9-oxo-1,8-diazatricyclo-[10.6.1.0$^{13,18}$]-nonadeca-12(19),13(18),14,16-tetraene (133 mg, 1 eq) there was obtained the crude benzyl ester after flash chromatography (3% MeOH/CH$_2$Cl$_2$). The crude benzyl ester was dissolved in THF/MeOH (1:1, 6 mL) and hydrolyzed with 1 M barium hydroxide (0.9 mL) overnight. Carbon dioxide was passed over the solution and the resulting precipitate was filtered off. The filtrate was concentrated and the aqueous residue was adjusted to pH 5.5 with 1 M HCl. Reverse phase HPLC afforded (2R,10S)-N'-(carboxymethyl)-amino- 4-methyl-N-(9-oxo-1,8-diazatricyclo[10.6.1.0$^{13,18}$]nonadeca-12(19), 13(18),14,16-tetraen-10-yl)pentanamide (17 mg) as a white solid, MS(FAB): 457 (MH$^+$).

EXAMPLE 40

Compounds of Formula (6)

4-Methyl-2-Methylenepentanoic Acid

A. To neat ethyl isobutylmalonate (25 g, 0,13 mol) at 0° was slowly added ice cold diethylamine (15.1 mL, 0.15 mol). After stirring for 15 min, formalin (11,1 mL 37% aqueous formaldehyde) was added dropwise. The mixture was allowed to stir at 250 for 3 days. The reaction mixture was then treated with a solution of 20 g of K$_2$CO$_3$ in 40 mL of water and extracted with ether (2×100 mL). The ether extracts were combined, washed with brine, dried over MgSO$_4$ and concentrated under reduced pressure at 20°.

The crude product, ethyl 4-methyl-2-methylenepentanoate containing some ether, was dissolved in absolute ethanol (250 mL) and treated with acetonitrile (250 mL), 1 M LiOH (9.7 g in 250 mL of water, 0.23 mol). After stirring overnight, the organic solvents were evaporated under reduced pressure and the aqueous residue was extracted with ethyl acetate (2×150 mL). The combined extracts were washed with brine, dried over MgSO$_4$ and concentrated under reduced pressure to afford 10.5 g of 4-methyl-2-methylenepentanoic acid as a colorless oil.

B. In a similar manner, the following compounds of formula (Gd) are prepared:
4-Phenyl-2-methylenebutanoic acid;
3-Cyclohexyl-2-methylenepropanoic acid;
5-Phenyl-2-methylenepentanoic acid;
2-Methylenepentanoic acid; and
3,3-dimethyl-2-methylenebutanoic acid.

EXAMPLE 41

Compound of Formula (Id)

(Reverse Hydroxamate)

A. A solution of 4-methyl-2-methylenepentanoic acid (3.5 g) and O-benzylhydroxylamine were heated at 1200 for 8 h. The reaction mixture was then partitioned between 50 mL of 1.0 N NaOH and 50 mL of diethyl ether. The aqueous portion was separated, acidified to pH 3 with 10% HCl and washed with 50 mL of ether. Ion exchange chromatography (Dowex—50W) eluting with 20% pyridine/water gave 2-(benzyloxyaminomethyl)-4-methylpentanoic acid.
300 MHz $^1$H NMR in CDCl$_3$: δ 0.9–1.0 (dd, 6H,CH$_3$); 1,25–1,35 (m, 1H, CH); 1,6–1,75 (m, 2H, CH$_2$); 2.8–2.9 (m, 1H, C$_a$—H); 3.0–3.2 (AB$_q$, 2H, CH$_2$N); 4.7–4.75 (AB$_q$, 2H, CH$_2$O); 7.3–7.4 (m, 5H, Ph).

B. Formylation of 2-(benzyloxyaminomethyl)-4-methylpentanoic acid was carried out in dichloromethane with formic acid/acetic anhydride to give N-formyl-2-(benzyloxyaminomethyl)-4-methylpentanoic acid. Coupling with a compound of formula (J): To N-formyl-2-(benzyloxyamino-methyl)-4-methylpentanoic acid (175 mg) and (J) (230 mg) in 5% pyridine/dichloromethane (30 mL) was added 4-dimethylaminopyridine (DMPA) (200 mg) and 1-(3-dimethylaminopropyl)-3-ethyl-carbodiimide hydrochloride (EDCI) at room temperature. The reaction mixture was stirred for 8 h and then concentrated, partitioned between 30 mL of ethyl acetate and 30 mL of 20% HCl. The organic portion was washed with water (20 mL), 5% NaHCO$_3$ (20 mL) and brine, dried over MgSO$_4$ and concentrated. Purification on silica gel, eluting with 50% ethyl acetate/hexane gave the product as a mixture of two isomers. Hydrogenolysis in methanol over 10% Pd/C afforded (2RS, 10S)-2-[N-formyl, N-hydroxyaminomethyl]-4-methyl-(9-oxo-1,8-diaza-tricyclo[10.6.1.0$^{13,18}$]nonadeca-12(19)13(18),14,6-tetraen-10-yl]pentamide, as a mixture of 2 isomers, MS 455 (M–H)$^+$, (Compound 6).
In a similar manner were prepared:
(2RS, 10S)-2-[iso-propoxycarbonylmethyl]-4-methyl-(9-oxo-1,8-diaza-tricyclo[10.6.1.0$^{13,18}$]nonadeca-12(19)13(18),14,6-tetraen-10-yl]pentamide, MS 455 (M+H)$^+$.

(2RS, 10S)-2-[morpholinocarbethoxymethyl]-4-methyl-(9-oxo-1,8-diaza-tricyclo[10.6.1.0$^{13,18}$]nonadeca-12(19)13 (18),14,6-tetraen-10-yl]pentamide, MS 555 (M+H)$^+$.

EXAMPLE 42

Compound of Formula (Iq)

A. Preparation of Formula (PP)

To a mixture of 2-(phthalimid-2-ylmethyl)-3(R)-isobutylsuccinic acid t-butyl ester (3.4 g), N-methylmorpholine (1.92 ml), 1-hydroxybenzotriazole (1.3 g) and (10S)-10-amino-(9-oxo-1,8-diazatricyclo [10.6.1.0$^{13,18}$]nonadeca-12(19),13(18),14,16-tetraene (2.49 g) in dry DMF (200 mL) at 0° C. under argon was added EDCI (3.34 g). The resulting mixture was stirred overnight, allowing the mixture to rise to ambient temperature, and the solvent then removed at 45° C. under high vacuum. The residue was stirred vigorously with a mixture of ethyl acetate (300 mL) and 0.5N hydrochloric acid (150 ml). The organic layer was washed with 0.5N HCl (2×150 ml), saturated NaHCO$_3$ (2×150 ml) and finally with brine (1×150 ml). After drying the organic layer over MgSO$_4$, it was filtered and evaporated to dryness. Purification of the residue by flash column chromatography (10% ethyl acetate/methylene chloride) gave (3R,10S)-2-(phthalimid-2-ylmethyl)-5-methyl-3-(9-oxo-1,8-diaza-tricyclo[10.6.1.0$^{13,18}$]nonadeca-12(19),13(18),14,16-tetraen-10-ylcarbamoyl) hexanoic acid t-butyl ester (4.81 g). This compound was obtained as 2.96 g of a less polar diasteroisomer, 1.05 g of a more polar diasteroisomer, and 0.8 g of a mixture of the two.

A. Preparation of Formula (Iq)

To a solution of the less polar isomer of the compound of formula (PP) prepared in 42A (2.96 g) in methanol (50 ml) and methylene chloride (50 ml) at room temperature was added hydrazine (2.8 ml). The mixture was stirred overnight, then a further 200 ml of methylene chloride and 300 ml of methanol added, followed by silica gel. The solvent was then removed under reduced pressure, and the residue of silica gel on which the material was adsorbed was loaded onto a silica gel column and flash chromatographed. Elution with 4% methanol/methylene chloride gave 2.01 g of (3R,10S)-2-(aminomethyl)-5-methyl-3-(9-oxo-1,8-diaza-tricyclo [10.6.1.0$^{13,18}$]nonadeca-12(19),13(18),14,16-tetraen-10-ylcarbamoyl)hexanoic acid t-butyl ester (4.81 g).

B. Hydrolysis of the ester with trifluoroacetic acid as shown below gave (3R,10S)-2-(aminomethyl)-5-methyl-3-(9-oxo-1,8-diaza-tricyclo[10.6.1.0$^{13,18}$]nonadeca-12 (19),13(18),14,16-tetraen-10-ylcarbamoyl)hexanoic acid, MS 471 (MH$^+$).

EXAMPLE 43

Compound of Formula (Ir)

A. To a solution of (3R,10S)-2-(aminomethyl)-5-methyl-3-(9-oxo-1,8-diaza-tricyclo [10.6.1.0$^{13,18}$]nonadeca-12 (19), 13 (18),14,16-tetraen-10-ylcarbamoyl)hexanoic acid t-butyl ester (363 mg) and triethylamine (0.54 ml) in dry methylene chloride (20 ml) at 0° C. was added methanesulfonyl chloride (77 µml). The resulting mixture was stirred for 2 hours, allowing the mixture to rise to ambient temperature, then methylene chloride (100 ml) and 0.5N hydrochloric acid (50 ml) added, stirring vigorously. The aqueous layer was further extracted with methylene chloride (2×75 ml), then the combined organic layers washed with brine (100 ml). After drying the organic layer over MgSO$_4$, it was filtered and evaporated to dryness. Purification of the residue by flash column chromatography (20–30% ethyl acetate/methylene chloride) gave (3R,10S)-2-(methylsulfonamidoaminomethyl)-5-methyl-3-(9-oxo-1,8-diaza-tricyclo[10.6.1.0$^{13,18}$]nonadeca-12(19),13(18),14,16-tetraen-10-ylcarbamoyl)hexanoic acid t-butyl ester as a white solid (211 mg).

B. To a solution of the compound obtained in A (180 mg) in methylene chloride (4 ml) at 0° C. was added trifluoroacetic acid (2 ml). The resulting mixture was stirred for 5 hours, allowing the mixture to rise to ambient temperature. The solvent was removed under reduced pressure, ethyl acetate was added to the residue, and the solution washed with water (7×30 ml). After drying the organic layer over MgSO$_4$, it was filtered and evaporated to dryness. Crystallization of the residue from methanol/ethyl acetate/hexanes gave (3R,10S)-2-(methylsulfonamidoaminomethyl)-5-methyl-3-(9-oxo-1,8-diaza-tricyclo[10.6.1.0$^{13,18}$]nonadeca-12(19),13(18),14, 16-tetraen- 10-ylcarbamoyl)hexanoic acid as a white solid (129 mg).

C. In a similar manner, the following compounds of formula (Ir) were prepared:

(3R,10S)-2-(methoxycarbonylaminomethyl)-5-methyl-3-(9-oxo-1,8-diazatricyclo[10.6.1.0$^{13,18}$]nonadeca-12(19), 13(18),14,16-tetraen-10-ylcarbamoyl)hexanoic acid, MS 527.5 (M–H$^+$);

(3R,10S)-2-(ethoxycarbonylaminomethyl)-5-methyl-3-(9-oxo-1,8-diazatricyclo[10.6.1.0$^{13,18}$]nonadeca-12(19),13 (18),14,16-tetraen-10-ylcarbamoyl)hexanoic acid, MS 541.5 (M–H$^+$);

(3R,10S)-2-(methanesulfonamidomethyl)-5-methyl-3-(9-oxo-1,8-diazatricyclo-[10.6.1.0$^{13,18}$]nonadeca-12(19),13 (18),14,16-tetraen-10-ylcarbamoyl)-hexanoic acid, MS 549.2 (M–H$^+$);

(3R,10S)-2-(ethanesulfonamidomethyl)-5-methyl-3-(9-oxo-1,8-diazatricyclo-[10.6.1.0$^{13,18}$]nonadeca-12(19),13(18), 14,16-tetraen-10-ylcarbamoyl)-hexanoic acid, MS 563 (M–H$^+$);

(3R,10S)-2-(trifluoromethanesulfonamidomethyl)-5-methyl-3-(9-oxo-1,8-diazatricyclo-[10.6.1.0$^{13,18}$] nonadeca-12(19),13(18),14,16-tetraen-10-ylcarbamoyl) hexanoic acid, MS 603.3 (M–H$^+$);

(3R,10S)-2-(phenylsulfonamidomethyl)-5-methyl-3-(9-oxo-1,8-diazatricyclo-[10.6.1.0$^{13,18}$]nonadeca-12(19),13 (18),14,16-tetraen-10-ylcarbamoyl)hexanoic acid, MS 611.1 (M–H$^+$);

(3R,10S)-2-(benzylsulfonamidomethyl)-5-methyl-3-(9-oxo-1,8-diazatricyclo-[10.6.1.0$^{13,18}$]nonadeca-12(19),13 (18),14,16-tetraen-10-ylcarbamoyl)hexanoic acid, MS 625.2 (M–H$^+$);

(3R,10S)-2-[5-(2-pyridyl)thiophen-2-ylsulfonamidomethyl]-5-methyl-3-(9-oxo-1,8-diazatricyclo-[10.6.1.0$^{13,18}$]nonadeca-12(19),13(18),14, 16-tetraen-10-ylcarbamoyl)hexanoic acid, MS 692.4 (M–H$^+$);

(3R,10S)-2-(imidazol-4-ylsulfonamidomethyl)-5-methyl-3-(9-oxo-1,8-diazatricyclo[10.6.1.0$^{13,18}$]nonadeca-12(19), 13(18),14,16-tetraen-10-ylcarbamoyl)hexanoic acid, MS 612.7 (M–H$^+$);

(3R,10S)-2-(thien-2-ylsulfonamidomethyl)-5-methyl-3-(9-oxo-1,8-diazatricyclo[10.6.1.0$^{13,18}$]nonadeca-12(19),13 (18),14,16-tetraen-10-ylcarbamoyl)hexanoic acid, MS 617.5 (M–H$^+$);

(3R,10S)-2-(2-phenylvinylsulfonamidomethyl)-5-methyl-3-(9-oxo-1,8-diazatricyclo[10.6.1.0$^{13,18}$]nonadeca-12(19), 13(18),14,16-tetraen-10-ylcarbamoyl)hexanoic acid, MS 637.6 (M–H$^+$);

(3R,10S)-2-(1-azanaphthyridin-8-ylsulfonamidomethyl)-5-methyl-3-(9-oxo-1,8-diazatricyclo-[10.6.1.0$^{13,18}$] nonadeca-12(19),13(18),14,16-tetraen-10-ylcarbamoyl) hexanoic acid, MS 549.2 (M–H$^+$);

(3R,10S)-2-(3-ethylureidomethyl)-5-methyl-3-(9-oxo-1,8-diazatricyclo-[10.6.1.0$^{13,18}$]nonadeca-12(19),13(18),14,16-tetraen-10-ylcarbamoyl)hexanoic acid, MS 542.34 (M–H$^+$); and (3R,10S)-2-(acetylaminomethyl)-5-methyl-3-(9-oxo-1,8-diazatricyclo-[10.6.1.0$^{13,18}$]nonadeca-12(19),13(18),14,16-tetraen-10-ylcarbamoyl)hexanoic acid, MS 512 (M–H$^+$);

Similarly prepared is:

(3R,9S)-2-(methanesulfonamidomethyl)-4-cyclopentyl-3-(8-oxo-1,7-diazatricyclo[9.6.1.0$^{12,17}$]octadeca-11(18),12(17), 13,15-tetraen-9-ylcarbamoyl)butanoic acid.

EXAMPLE 44

This example illustrates the preparation of representative pharmaceutical compositions for oral administration containing a compound of formula (I), or a pharmaceutically acceptable salt thereof, e.g., (3R,10S)-N-hydroxy-5-methyl-3-(9-oxo-1,8-diazatricyclo[10.6.1.0$^{13,18}$]-nonadeca-12(19),13(18),14,16-tetraen-10-ylcarbamoyl)hexanamide:

| Ingredients | % wt./wt. |
| --- | --- |
| Compound of formula (I) | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| Ingredients | % wt./wt. |
| --- | --- |
| Compound of formula (I) | 20.0% |
| Magnesium stearate | 0.9% |
| Starch | 8.6% |
| Lactose | 79.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| Ingredients | |
| --- | --- |
| Compound of formula (I) | 0.1 g |
| Propylene glycol | 20.0 g |
| Polyethylene glycol 400 | 20.0 g |
| Polysorbate 80 | 1.0 g |
| Water | q.s. 100 mL |

The compound of formula (I) is dissolved in propylene glycol, polyethylene glycol 400 and polysorbate 80. A sufficient quantity of water is then added with stirring to provide 100 mL of the solution which is filtered and bottled.

| Ingredients | % wt./wt. |
| --- | --- |
| Compound of formula (I) | 20.0% |
| Peanut Oil | 78.0% |
| Span 60 | 2.0% |

The above ingredients are melted, mixed and filled into soft elastic capsules.

EXAMPLE 45

This example illustrates the preparation of a representative pharmaceutical formulation for parenteral administration containing a compound of formula (I), or a pharmaceutically acceptable salt thereof, e.g., (3R,11S)-N-hydroxy-5-methyl-3-(10-oxo-1,9-diazatricyclo-[11.6.1.0$^{14,19}$]eicosa-13(20),14(19),15,17-tetraen-11-ylcarbamoyl)hexanamide:

| Ingredients | |
| --- | --- |
| Compound of formula (I) | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of formula (I) is dissolved in propylene glycol, polyethylene glycol 400 and polysorbate 80. A sufficient quantity of 0.9% saline solution is then added with stirring to provide 100 mL of the I.V. solution which is filtered through a 0.2 $\mu$ membrane filter and packaged under sterile conditions.

EXAMPLE 46

This example illustrates the preparation of a representative pharmaceutical composition in suppository form containing a compound of formula (I), or a pharmaceutically acceptable salt thereof, e.g., (10S)-2-mercaptomethyl-4-methyl-N-(9-oxo-1,8-diazatricyclo-[10.6.1.0$^{13,18}$]nonadeca-12(19),13(18),14,16-tetraen-10-ylcarbamoyl)pentanamide:

| Ingredients | % wt./wt. |
| --- | --- |
| Compound of formula (I) | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 47

This example illustrates the preparation of a representative pharmaceutical formulation for insufflation containing a compound of formula (I), or a pharmaceutically acceptable salt thereof, e.g., (10S)-4-methyl-2-(9-oxo-1,8-diazatricyclo-[10.6.1.0$^{13,18}$]nonadeca-12(19),13(18), 14,16-tetraen-10-ylcarbamoyl)pentyl-(quinolin-2-ylthiomethyl)phosphinic acid:

| Ingredients | % wt./wt. |
| --- | --- |
| Micronized compound of formula (I) | 1.0% |
| Micronized lactose | 99.0% |

The ingredients are milled, mixed, and packaged in an insufflator equipped with a dosing pump.

EXAMPLE 48

This example illustrates the preparation of a representative pharmaceutical formulation in nebulized form containing a compound of formula (I), or a pharmaceutically acceptable salt thereof, e.g., (3R,10S)-N-hydroxy-5-methyl- 3-(9-oxo-1,8-diazatricyclo-[10.6.1.0$^{13,18}$]nonadeca-12(19), 13(18),14,16-tetraen-10-ylcarbamoyl)hexanamide:

| Ingredients | % wt./wt. |
| --- | --- |
| Compound of formula (I) | 0.005% |
| Water | 89.995% |
| Ethanol | 10.000% |

The compound of formula (I) is dissolved in ethanol and blended with water. The formulation is then packaged in a nebulizer equipped with a dosing pump.

EXAMPLE 49

This example illustrates the preparation of a representative pharmaceutical formulation in aerosol form containing a compound of formula (I), or a pharmaceutically acceptable salt thereof, e.g., (3R,11S)-N-hydroxy-5-methyl-3-(10-oxo-1,9-diazatricyclo[$11.6.1.0^{14,19}$]eicosa-13(20),14(19),15,17-tetraen-11-ylcarbamoyl)hexanamide:

| Ingredients | % wt./wt. |
|---|---|
| Compound of formula (I) | 0.10% |
| Propellant 11/12 | 98.90% |
| Oleic acid | 1.00% |

The compound of formula (I) is dispersed in oleic acid and the propellants. The resulting mixture is then poured into an aerosol container fitted with a metering valve.

EXAMPLE 50

In Vitro Assay

Fibroblast type I collagenase was purified from the serum-free culture medium of GM00010A cells, stimulated with PMA, by heparin and zinc-chelating sepharose columns followed by FPLC (MONO S column). The enzyme was activated by incubation with trypsin.

Type IV collagenase was purified from the serum-containing culture medium of fibroblast (GMOO1OA) cells by zinc-chelating and gelatin-sepharose columns, followed by FPLC (MONO S column). The enzyme was shown to be homogeneous by SDS-PAGE. The enzyme was activated by incubation with 1 mmol APHA for 1 hr at 35–37° C.

Compounds of formula (I) were dissolved in DMSo and added to a cuvette containing 0.2 $\mu$g Type I or 0.03 $\mu$g Type IV collagenase in 1 ml TC buffer (20 mM Tris, 5 mM $CaCl_2$, pH 7.5) (2% DMSO final concentration). The concentrations of the compounds of formula (I) were chosen such that there was at least one data point for every 20% change in activity. Enzyme and compounds were permitted to pre-incubate 3 min at 37° C. To initiate the reaction, N-(7-dimethylamino-4-methyl)coumarinyl ("DACM") (Sigma) and thiopeptide (Ac-Pro-Leu-Gly-5-"Leu"-Leu-Gly-OEt, Bachem Bioscience Inc.) were added to 20 uM each. The fluorescence was recorded with excitation and emission wavelengths of 395 and 485 nm, respectively. Each data point is the average of duplicate experiments. At least six data points, expressed as change in fluorescence per minute versus compound concentration were analyzed using the IC50 fit in the program, Enzfitter.

Compounds of formula (I) exhibited the ability to inhibit the collagenases when tested in this assay.

EXAMPLE 51

In Vitro Assay

This assay determines if the compounds of formula (I) inhibit the release of $^{35}$S-labelled glycosaminoglycans (GAG's) from cartilage explants.

Small cartilage explants (3 mm diameter) were prepared from freshly sacrificed bovine knee joints and labeled with $^{35}SO_4$. $^{35}$S-labelled glycosaminoglycans (GAG's) are released into the culture medium in response to the addition of rhIL-1-alpha, which induces the expression of chondrocyte matrix metalloproteases (MMP's), including stromelysin and collagenase. The percent inhibition of labeled GAG's was corrected for spontaneous release in the absence of rhlL-1-alpha. Results for each group represent the mean ± the S.E.M. for five explants.

Compounds of formula (I), when tested in this assay, displayed the ability to inhibit the release of $^{35}$S-labelled GAG's from cartilage explants.

EXAMPLE 52

In Vitro Assay

An in vitro fetal rat long bone model was used to study the anti-bone resorptive effect of the compounds of formula (I). Bovine PTH was used to induce bone resorption in vitro. The bone resorptive effects were expressed by the amounts of 4ca released from the $^{45}$Ca pre-labelled fetal rat long bones into the culture medium. The inhibitory effect of the compounds of formula (I) against bovine PTH induced bone resorption was expressed as mean percent inhibition ± sem.

$^{45}$Ca-prelabelled fetal rat long bones (from forearms) were dissected and cultured in Linbro dishes at 37° C. overnight BGJb medium, supplemented with 1 mg/ml BSA. There were five pairs of bones in each group. The compounds of formula (I) were dissolved in ethanol first, then diluted to various concentrations and added simultaneously with Bovine PTH (1–34) at $1 \times 10^8$M on Day 1. The ethanol concentrations in the compound solutions were less than 0.05% which did not interfere with the assay. The assay was terminated on Day 6 with one media change on Day 3.

At the end of each medium change, the $^{45}$Ca present in the culture medium was counted. The remaining bones were digested with 0.1N HCl and the $^{45}$Ca presented in the bone digest was also counted. The results are expressed as % of the total $^{45}$Ca released from each pair of bones. Bovine PTH at $1 \times 10^{-8}$M induces bone resorption to the maximum level which is set as 100% and this concentration was used as standard. The level of base line bone resorption in the presence of medium only was set as 0%. All compound-treated groups were compared with bovine PTH (1–34) at $1 \times 10^{-8}$M. The concentration at which a compound inhibited bone resorption by 50% was defined as $IC_{50}$.

The compounds of formula (Ia) exhibited the ability to inhibit bovine PTH-induced bone resorption in this assay.

What is claimed is:

1. A compound of formula as a single stereoisomer or (I) as a mixture of stereoisomers:

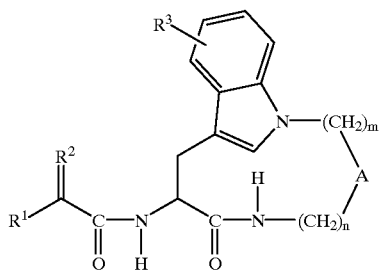

wherein:
 m is 3;
 n is 2;
 A is —CH$_2$;
 R$^1$ is —CH$_2$—R$^4$ where R$^4$ is carboxy, or alkoxycarbonyl;
 R$^2$ is alkyl having from 1 to 6 carbons, biphenylpropyl, thien-2yl-ethyl, cyclopentyl, cyclopropylmethyl, or cyclopentylmethyl; and
 R$^3$ is hydrogen.

2. A compound of formula as a single stereoisomer or (I) as a mixture of stereoisomers:

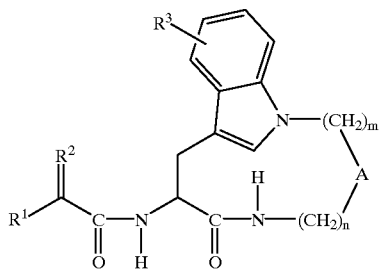

wherein:
 m is 3; and
 n is 1, 2, or 3;
 A is —CH$_2$—;
 R$^1$ is —CH$_2$R$^4$ where R$^4$ is carboxy, hydroxyaminocarbonyl, or N-hydroxyformylamino;
 R$^2$ is 2-methylpropyl; and
 R$^3$ is hydrogen.

3. A compound of formula (I) as a single stereoisomer or as a mixture of stereoisomer:

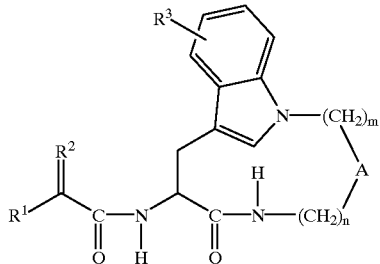

wherein:
 m is 3; and
 n is 1, 2, or 3;
 A is —CH$_2$—;
 R$^1$ is —CH$_2$—R$^4$ where R$^4$ is mercapto or acetylthio;
 R$^2$ is 2-methylpropyl; and
 R$^3$ is hydrogen.

4. A compound of formula as a single stereoisomer or (I) as a mixture of stereoisomers:

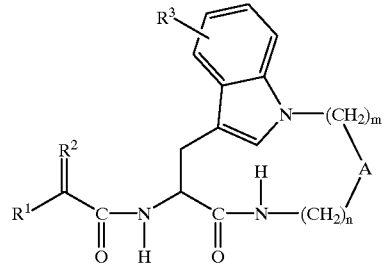

wherein:
 m is 3; and
 n is 2;
 A is —CH$_2$—;
 R$^1$ is —CH(CH$_2$NHR)—R$^8$— where R$^8$ is carboxy and R is hydrogen, —C(O)OR$^a$, —SO$_2$R$^a$ or —C(O)NHR$^a$ where R$^a$ is alkyl having from 1 to 6 carbons;
 R$^2$ is 2-methylpropyl; and
 R$^3$ is hydrogen.

5. The 3R,10S stereoisomer of the compound or salt of claim 1 wherein R$^2$ is biphenylpropyl; and R$^4$ is carboxy; namely (3R,10S)-6-(biphenyl-4-yl)-3-(9-oxo-1,8-diazatricyclo[10.6.1.0$^{13,18}$]nonadeca-12(19),13(18),14,16-tetraen-10-ylcarbamoyl)hexanoic acid.

6. The 3R,10S stereoisomer of the compound or salt of claim 1 wherein R$^2$ is thien-2-ylethyl; and R$^4$ is carboxy; namely (3R,10S)-3-(9-oxo-1,8-diazatricyclo[10.6.1.0$^{13,18}$] nonadeca12(19), 13(18),14,16-tetraen-10-ylcarbamoyl)-5-(thiophen-2-yl)pentanoic acid.

7. The 3R,10S stereoisomer of the compound or salt of claim 1 wherein R$^2$ is cyclopentyl; and R$^4$ is carboxy; namely (3R,10S)-3-cyclopentyl-3-(9-oxo-1,8-diazatricyclo[10.6.1.0$^{13,18}$]-nonadeca12(19), 13(18),14,16tetraen-10-ylcarbamoyl)propionic acid.

8. The 3R,10S stereoisomer of the compound or salt of claim 1 wherein R$^2$ is cyclopentylmethyl; and R$^4$ is carboxy; namely (3R,10S)-4-cyclopentyl-3-(9-oxo-1,8-diazatricyclo[10.6.1.0$^{13,18}$]-nonadeca12(19),13(18),14,16-tetraen-10-ylcarbamoyl)butanoic acid.

9. The 3R,10S stereoisomer of the compound or salt of claim 1 wherein R$^2$ is cyclopropylmethyl; and R$^4$ is carboxy; namely (3R,10S)-4-cyclopropyl-3-(9-oxo-1,8-diazatricyclo[10.6.1.0$^{13,18}$]-nonadeca12(19),13(18),14,16-tetraen-10-ylcarbamoyl)butanoic acid.

10. The 3R,10S stereoisomer of the compound or salt of claim 2 wherein n is 2; and R$^4$ is carboxy; namely (3R, 10S)-5-methyl-3-(9-oxo-1,8-diazatricyclo-[10.6.1.0$^{13,18}$] nonadeca-12(19),13(18),14,16-tetraen-10-ylcarbamoyl) hexanoic acid.

11. The 3R,10S stereoisomer of the compound or salt of claim 2 wherein n is 2; and R$^4$ is N-hydroxyaminocarbonyl; namely (3R,10S)-N-hydroxy-5-methyl-3-(9-oxo-1,8-diazatricyclo-[10.6.1.0$^{13,18}$]-nonadeca-12(19),13(18),14, 16-tetraen-10-ylcarbamoyl)hexanamide.

12. The 3R,11S stereoisomer of the compound of claim 2 wherein; n is 3; and $R^4$ is N-hydroxyaminocarbonyl; namely (3R,11S)-N-hydroxy-5-methyl-3-(10-oxo-1,9-diazatricyclo[11.6.1.0$^{14,19}$]eicosa-13(20),14(19),15,17-tetraen-11-ylcarbamoyl)hexanamide.

13. The 3R,9S stereoisomer of the compound of claim 2 wherein n is 1; and $R^4$ is carboxy; namely (3R,9S)-5-methyl-3-(8-oxo-1,7-diazatricyclo-[9.6.1.0$^{12,17}$]octadeca-11(18),12(17),13,15-tetraen-9-ylcarbamoyl)hexanoic acid.

14. The 3R,9S stereoisomer of the compound of claim 2 wherein n is 1; and $R^4$ is N-hydroxyaminocarbonyl; namely (3R,9S)-N-hydroxy-5-methyl-3-(8-oxo-1,7-diazatricyclo-[9.6.1.0$^{12,17}$]octadeca-11(18),12(17),13,15-tetraen-9-ylcarbamoyl)hexanamide.

15. The (10S) stereoisomer of compound or salt of claim 3 wherein n is 2 and $R^4$ is mercapto, namely (10S)-2-mercaptomethyl-4-methyl-N-(9-oxo-1,8-diazatricyclo-[10.6.1.0$^{13,18}$]nonadeca-12(19),13(18),14,16-tetraen-10-ylcarbamoyl)pentanamide.

16. The (10S) stereoisomer of compound or salt of claim 3 wherein n is 2 and $R^4$ is acetylthio, namely (10S)-2-acetylthiomethyl-4-methyl-N-(9-oxo-1,8-diazatricyclo[10.6.1.0$^{13,18}$]nonadeca-12(19),13(18),14,16-tetraen-10-ylcarbamoyl)pentanamide.

17. (10S)-[4-methyl-2-(9-oxo-1,8-diazatricyclo[10.6.0$^{13,18}$]nonadeca-12(19),13(18),14,16-tetraen-10-ylcarbamoyl)pentanamido]-(quinolin-2-ylthiomethyl)phosphinic acid.

18. The 3R,10S stereoisomer of the compound or salt of claim 4 wherein R is hydrogen, namely (3R,10S)-2-(aminomethyl)-5-methyl-3-(9-oxo-1,8-diazatricyclo[10.6.1.0$^{13,18}$] nonadeca-12(19),13(18),4,16-tetraen-10-ylcarbamoyl)hexanoic acid.

19. The 3R,10S stereoisomer of the compound or salt of claim 4 wherein R is —C(O)OCH$_3$, namely (3R,10S)-2-(methoxycarbonylaminomethyl)-5-methyl-3-(9-oxo-1,8-diazatricyclo-[10.6.1.0$^{13,18}$]nonadeca-12(19),13(18),14,16-tetraen-10-ylcarbamoyl)hexanoic acid.

20. The 3R,10S stereoisomer of the compound or salt of claim 4 wherein R is —SO$_2$CH$_3$, namely (3R,10S)-2-(methanesulfonamidomethyl)-5-methyl-3-(9-oxo-1,8-diazatricyclo-[10.6.1.0$^{13,18}$]nonadeca-12(19),13(18),14,16-tetraen-10-ylcarbamoyl)hexanoic acid.

21. The 3R,10S stereoisomer of the compound or salt of claim 4 wherein R is —C(O)NHCH$_2$CH$_3$, namely (3R,10S)-2-(3-ethylureidomethyl)-5-methyl-3-(9-oxo-1,8-diazatricyclo-[10.6.1.0$^{13,18}$]nonadeca-12(19),13(18),14,16-tetraen-10-ylcarbamoyl)hexanoic acid.

22. (3R,10S)-N-hydroxy-5-methyl-2-methoxycarbonyl-3-(9-oxo-1,8-diazatricyclo-[10.6.1.0$^{13,18}$]nonadeca-12(19),13(18),14,16-tetraen-10-ylcarbamoyl)hexanamide.

* * * * *

UNITED STATES PATENT AND TRADEMARK OFFICE
CERTIFICATE OF CORRECTION

PATENT NO. : 6,013,792
DATED : January 11, 2000
INVENTOR(S) : Castelhano et al.

It is certified that error appears in the above-identified patent and that said Letters Patent is hereby corrected as shown below:

Claim 1, column 58,
Line 66, "A compound of formula as a single sterioisomer or (I)" should read -- A compound of formula (I) as a single stereoisomer or --.

Claim 1, coulmn 59,
Line 23, "thien-2yl-ethyl, cyclopentyl, cyclopropylmethyl, or" should read -- thien 2-yl-ethyl, cyclopentyl, cyclopropylmethyl, or --.

Claim 2, column 59,
Line 24, "A compound of formula as a single sterioisomer or (I)" should read -- A compound of formula (I) as a single stereoisomer or --.
Line 47, "$R^1$ is $-CH_2R^4$ where $R^4$ is carboxy," should read -- $R^1$ is $-CH_2-R^4$ where $R^4$ is carboxy --.

Claim 4, column 60,
Line 7, "A compound of formula as a single sterioisomer or (I)" shold read -- A compound of formula (I) as a single stereoisomer or --.

Claim 7, column 60,
Line 46, "13(18),14,16tetraen-10-" should read -- 13(18),14,16-tetraen-10- --.

Claim 8, column 60,
Line 51, "-nonadeca12(19),13(18),14.16-tetraen-10" should read -- nonadeca12(19),13(18),14.16-tetraen-10- --.

Signed and Sealed this

Twenty-fifth Day of September, 2001

Attest:

NICHOLAS P. GODICI
*Attesting Officer*   Acting Director of the United States Patent and Trademark Office